United States Patent [19]

Nishigaki et al.

[11] Patent Number: 5,007,907
[45] Date of Patent: Apr. 16, 1991

[54] RESECTOSCOPE APPARATUS

[75] Inventors: Shinichi Nishigaki, Tokyo; Shiro Bito, Hachioji, both of Japan

[73] Assignee: Olympus Optical Co., Ltd., Tokyo, Japan

[21] Appl. No.: 254,741

[22] Filed: Oct. 7, 1988

[30] Foreign Application Priority Data

Oct. 7, 1987 [JP] Japan ................................ 62-254069

[51] Int. Cl.$^5$ .............................................. A61B 17/36
[52] U.S. Cl. ...................................................... 606/46
[58] Field of Search ........................ 606/41, 45, 46, 49

[56] References Cited

U.S. PATENT DOCUMENTS

| | | | |
|---|---|---|---|
| 2,545,865 | 3/1951 | Wallace | 606/46 |
| 3,752,159 | 8/1973 | Wappler | 606/46 |
| 3,856,015 | 12/1974 | Inglesias | 128/303.15 |
| 4,311,144 | 1/1982 | Harada | 606/46 |
| 4,724,836 | 2/1988 | Okada | 606/46 |
| 4,726,370 | 2/1988 | Karasawa et al. | 606/46 |

FOREIGN PATENT DOCUMENTS 60-149616 10/1985 Japan .
62-193803 11/1987 Japan .

*Primary Examiner*—Max Hindenburg
*Attorney, Agent, or Firm*—Armstrong, Nikaido, Marmelstein, Kubovcik & Murray

[57] ABSTRACT

The resectoscope apparatus comprises an elongate hollow sheath to be inserted into a body cavity, an electrode inserted through the sheath to make such treatments as of resecting and coagulating tissues within the body cavity by using a high frequency current, an operating part which can operate the electrode from outside the body, a cord for feeding a high frequency current to the electrode from a high frequency current source and an optical sighting tube inserted through the sheath and having an optical system which can observe the body cavity interior and the electrode is made integral at least on the rear end side with the cord. For example, the electrode has a shaft part connected at the rear end to the above mentioned operating part and inserted through the sheath and a tip electrode part provided at the tip of the shaft part and projected and retracted from the sheath tip. The operating part has a connecting part removably connectable to the sheath at the rear end and a slider connected with the electrode shaft part at the rear end and slidable in the axial direction. The resectoscope apparatus further comprises, for example, a connecting apparatus mechanically and removably connecting the electrode shaft part at the rear end to the slider.

8 Claims, 15 Drawing Sheets

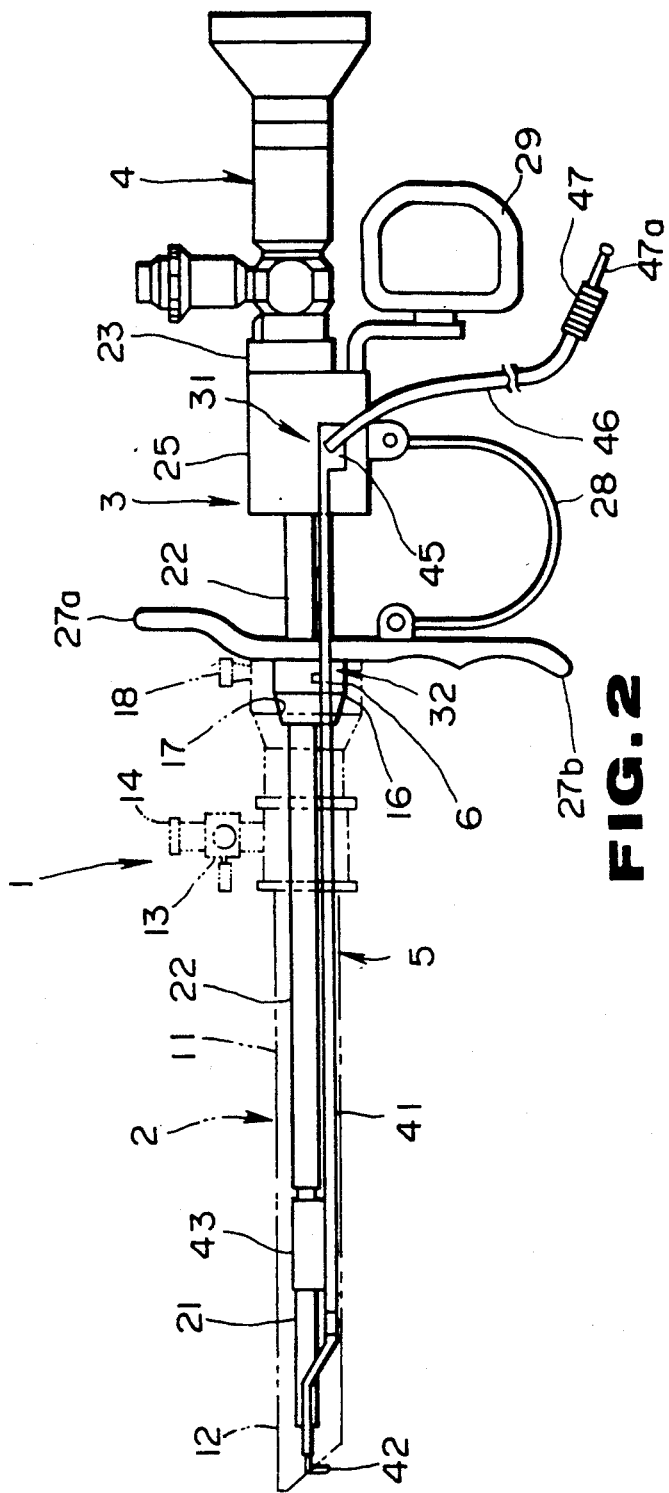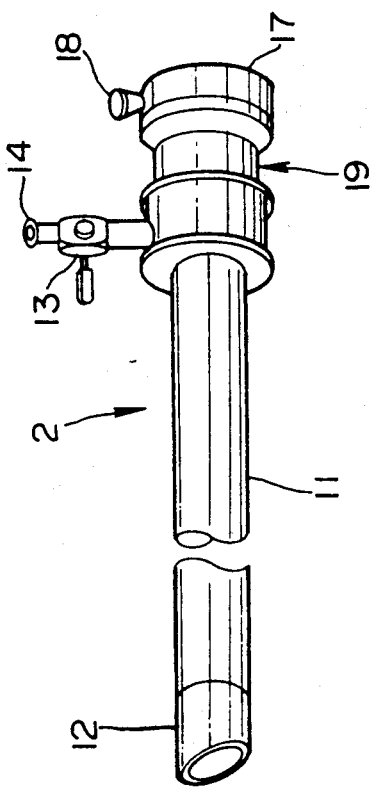

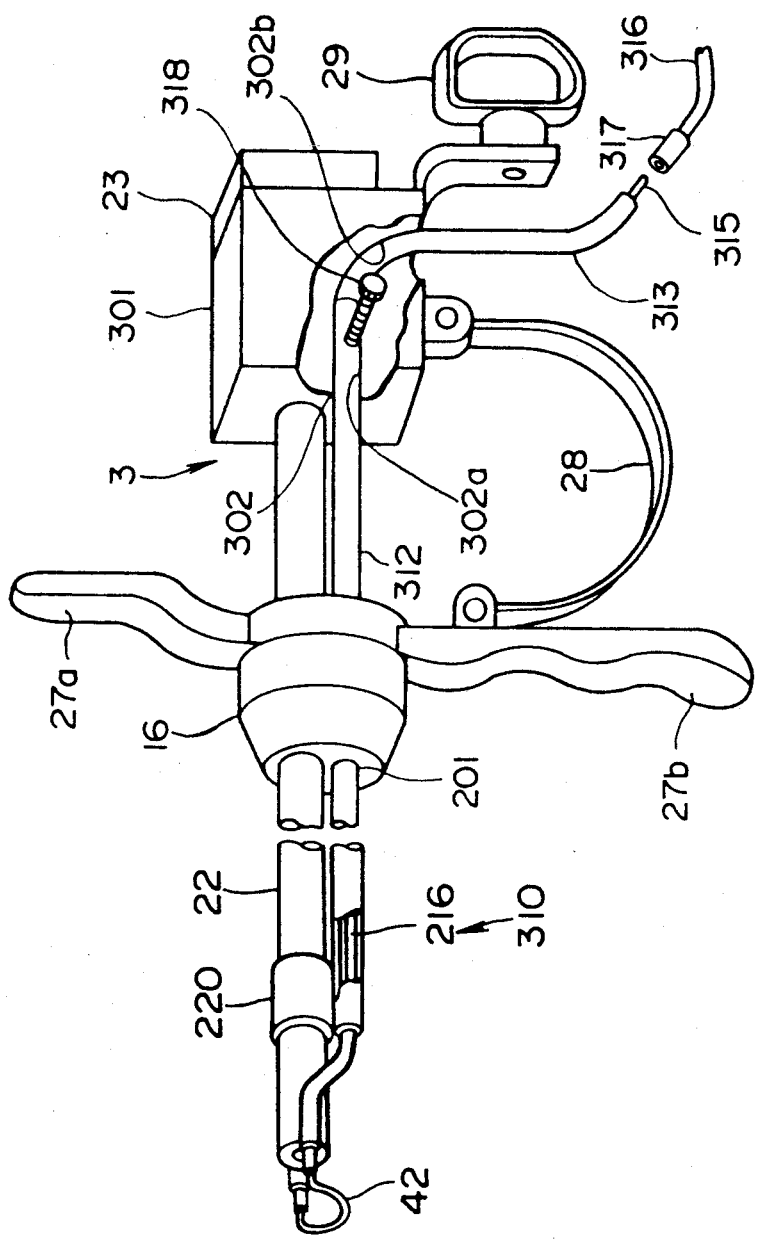

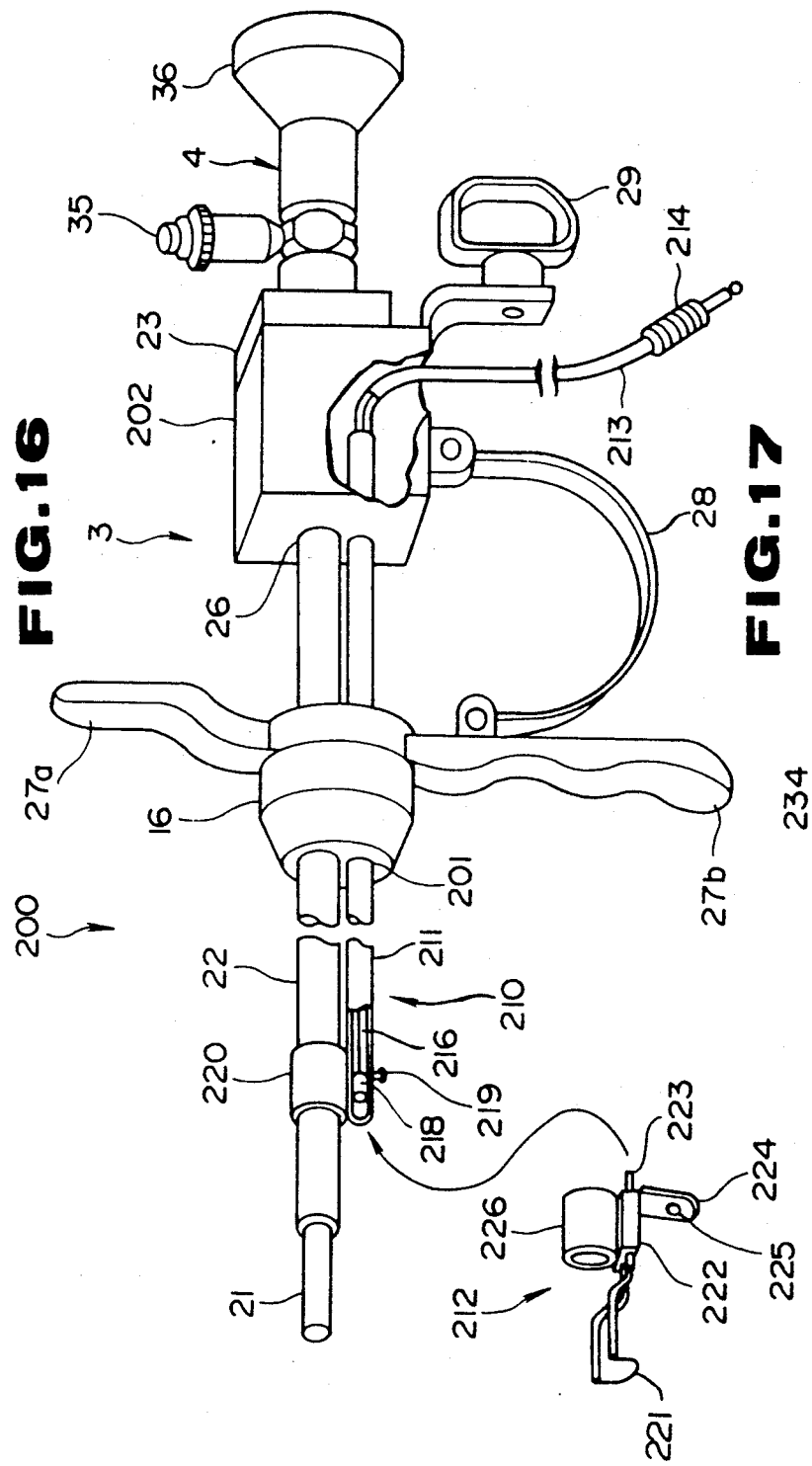

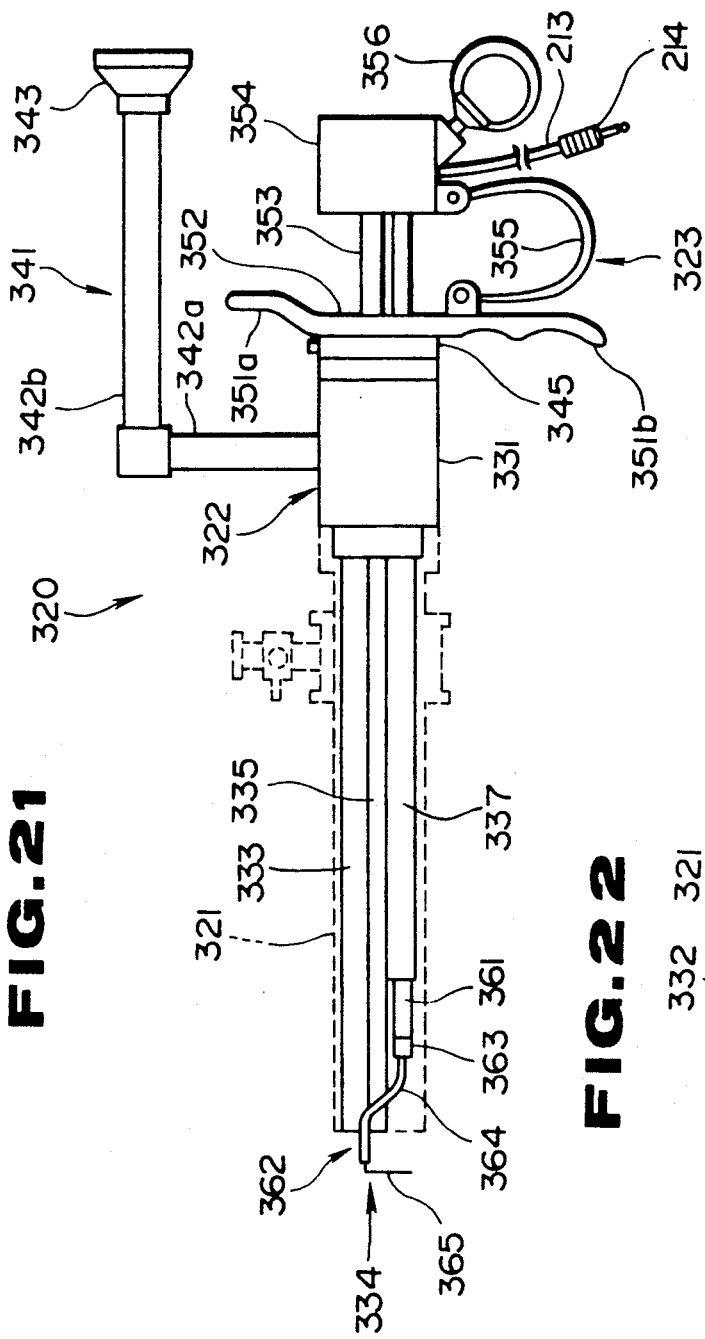

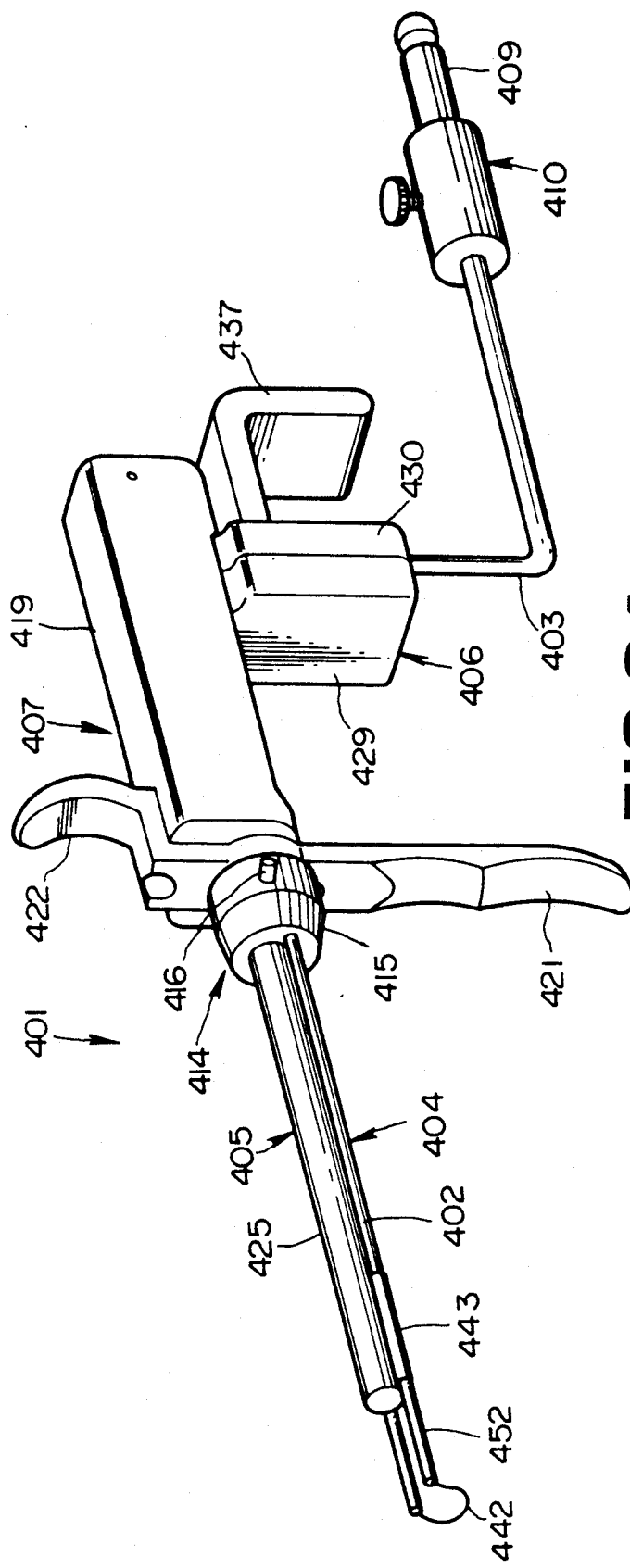

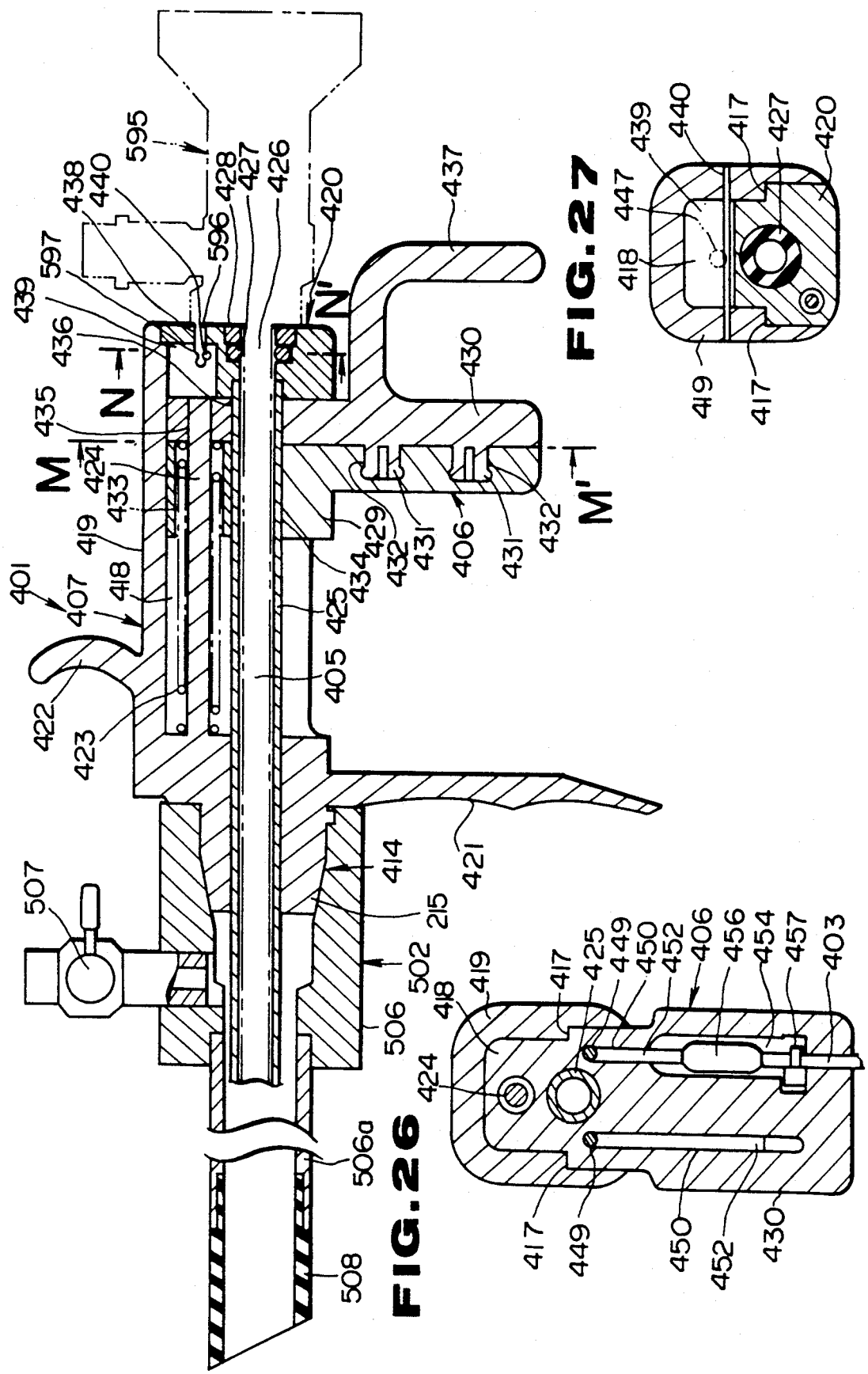

RESECTOSCOPE APPARATUS

BACKGROUND OF THE INVENTION

1. Field of the Invention

This invention relates to a resectoscope high in the electric safety and stability.

2. Related Art Statement

Recently, there are extensively utilized endoscope apparatus whereby organs within a body cavity can be observed by inserting an elongate insertable part into the body cavity or various therapeutic treatments can be made by using treating tools inserted, as required, through a treating tool channel.

High frequency endoscope apparatus for resecting a prostate gland, womb internal cavity, urethra interior, kidney interior and the like are among the above mentioned endoscope apparatus.

As shown, for example, in the publication of a Japanese utility model application laid open No. 149616/1985, one of such high frequency endoscope apparatus is a resectoscope which is inserted into a bladder through a urethra and is electrified with a high frequency current at a resecting electrode so that the prostate gland or the like may be resected.

Generally, a resectoscope apparatus comprises a hollow sheath to be inserted into a body cavity, an operating part having a slider removably fitted to this sheath at the rear end and an observing scope (optical sighting tube) removably fitted to this operating part from the rear end side so that an electrode branched to be forked like a loop at the tip to reset tissues within a body cavity may be projected and retracted from the above mentioned sheath tip.

In a conventional resectoscope apparatus, as shown in a Japanese utility model application laid open No. 183803/1987, the above mentioned electrode is removably fitted to the operating part, an electrical and mechanical fixing mechanism is provided within the above mentioned slider and a cord for feeding a high frequency current to the fixing mechanism from a current source is also removably fitted to a connector provided in the slider.

However, in case mechanisms for removably fitting an electrode and cord are in the slider, it will be difficult to secure the water-tightness of the connecting parts of the slider and electrode and of the slider and cord, the current will be likely to leak through the entering liquid and a burn or the like will be likely to be caused. Particularly, in case a sterilizing liquid containing a surface active agent is used, this liquid will be very likely to enter the connecting parts, form an electric circuit and leak the current.

Also, a blood, dirt and the like will be likely to enter the respective electric connecting parts, deteriorate the conduction of electricity and reduce the resecting capacity.

Further, there are problems that the respective mechanisms for removably fitting the electrode and cord will be separately required, the structure will be complicated and the slider will be large and breakable.

OBJECT AND SUMMARY OF THE INVENTION

An object of the present invention is to provide a resectoscope apparatus wherein an electric current leak and contact failure are eliminated and the electric safety and stability are improved.

Another object of the present invention is to provide a resectoscope apparatus wherein the electric safety and stability are improved and the mechanism for removably fitting the electrode can be made simple.

The resectoscope apparatus of the present invention comprises an elongate hollow sheath to be inserted into a body cavity, an electrode inserted through the above mentioned sheath to make such treatments as of resecting and coagulating tissues within the body cavity by using a high frequency current, an operating part which can operate the above mentioned electrode from outside the body, a cord for feeding a high frequency current to the above mentioned electrode from a high frequency current source and an optical sighting tube inserted through the above mentioned sheath and having an optical system which can observe the body cavity interior and the above mentioned electrode is made integral at least on the rear end side with the above mentioned cord. For example, the above mentioned electrode has a shaft part connected at the rear end to the above mentioned operating part and inserted through the above mentioned sheath and a tip electrode part provided at the tip of the above mentioned shaft part and projected and retracted from the above mentioned sheath tip by the operation of the above mentioned operating part. The above mentioned operating part has a connecting part removably connectable to the above mentioned sheath at the rear end and a slider connected with the above mentioned electrode shaft part at the rear end and slidable in the axial direction. The resectoscope apparatus is further provided, for example, with a connecting means mechanically removably connecting the above mentioned electrode shaft part at the rear end to the above mentioned slider.

The other features and advantages of the present invention will become apparent enough with the following explanation.

BRIEF DESCRIPTION OF THE DRAWINGS

FIGS. 1 to 7 relate to the first embodiment of the present invention.

FIG. 1 is a side view showing an entire resectoscope.

FIG. 2 is a perspective view of a sheath.

FIG. 3 is a perspective view of a handle incorporating an optical sighting tube.

FIG. 4 is a perspective view of an electrode device.

FIG. 5 is a perspective view of a rubber packing.

FIG. 6 is a perspective view showing an electrode device on the tip side in a modification of the first embodiment.

FIG. 7 is a sectioned view on line A—A in FIG. 6.

FIG. 8 is a partly sectioned perspective view showing a handle operating part.

FIG. 9 is a perspective view showing an electrode device on the base side.

FIG. 10 is a partly sectioned perspective view showing a handle operating part.

FIG. 11 is a perspective view of a packing.

FIG. 12 is a perspective view showing an electrode device on the base side.

FIG. 13 is a partly sectioned perspective view showing a handle operating part.

FIG. 14 is a perspective view showing an electrode device on the base side.

FIG. 15 is a perspective view showing a handle and electrode device in the fifth embodiment of the present invention.

FIG. 16 is a partly sectioned perspective view showing a resectoscope of the sixth embodiment of the present invention.

FIG. 17 is a perspective view showing a connecting part of an electrode part and electrode driving shaft in the seventh embodiment of the present invention.

FIGS. 21 and 22 relate to the 11th embodiment of the present invention.

FIG. 21 is a side view showing an entire resectoscope apparatus.

FIG. 22 is an elevation of a tip part in FIG. 21.

FIGS. 23 to 31 relate to the 12th embodiment of the present invention.

FIG. 23 is a perspective view of a resecting handle.

FIG. 24 is a perspective view of an optical sighting tube.

FIG. 25 is a longitudinally sectioned view of a resecting handle.

FIG. 26 is a sectioned view on line M—M' in FIG. 25.

FIG. 27 is a sectioned view on line N—N' in FIG. 25.

FIG. 28 is a side view of a resecting handle showing an electrode part as partly sectioned.

FIG. 29 is a sectioned view on line O—O' in FIG. 28.

FIG. 30 is a partly sectioned perspective view of an electrode part.

FIG. 31 is an elevation showing the position relations of an electrode tip loop, sheath and optical sighting tube as the sheath and optical sighting tube are combined.

DETAILED DESCRIPTION OF PREFERRED EMBODIMENTS

Figure 3:
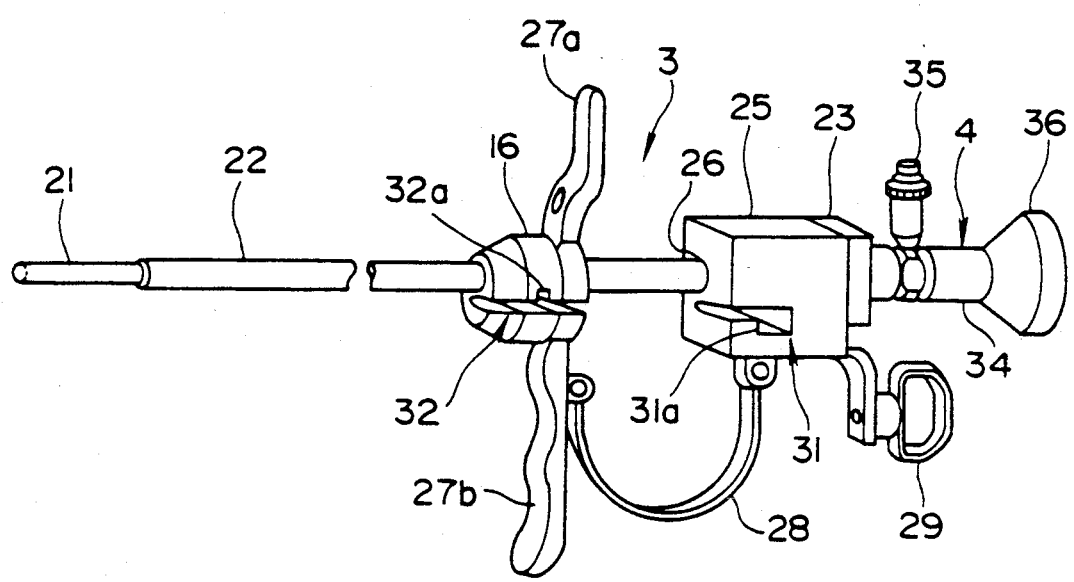

The first embodiment of the present invention is shown in FIGS. 1 to 7.

As shown in FIG. 1, a resectoscope 1 comprises a sheath 2 shown by two-point chain lines, a handle 3 connected to this sheath 2 at the rear end, an optical sighting tube 4 inserted through the sheath from this handle 3, an electrode device 5 inserted through the sheath 2 from the above mentioned handle 3 and a rubber packing 6 keeping the water-tightness between the above mentioned sheath 2 and handle 3.

As shown in FIG. 2, the above mentioned sheath 2 has an insertable pipe 11 formed to be elongate so as to be insertable into the urethra and an insulated beak 12 connected to this insertable pipe 11 at the tip. By the way, the above mentioned insertable pipe 11 may be formed of an insulating material integrally with the above mentioned insulated beak. The above mentioned insertable pipe 11 has on the base side a cock 13 fitted water feeding port 14, a fitting port 17 into which the above mentioned handle 3 can be fitted in the sheath connecting part 16 and a sheath body 19 provided with a removably fitted button 18 engaging and disengaging, for example, a clicking mechanism for fixing the above mentioned sheath connecting part 16 in the fitting part 17.

As shown in FIG. 3, in the above mentioned handle 3, an optical sighting tube guide pipe 22 through which the insertable part 21 of the above mentioned optical sighting tube 4 is inserted is fitted and connected to the above mentioned sheath connecting part 16 and is to be inserted on the tip side into the above mentioned sheath 2. On the other hand, the above mentioned optical sighting tube guide pipe 22 is projected on the rear end side rearward of the above mentioned sheath connecting part 16 and is provided at the rear end with an optical sight tube connecting part 23 in which the above mentioned optical sighting tube 4 can be removably inserted and connected.

A slider 25 sliding in the axial direction along the above mentioned optical sighting tube guiding pipe 22 is arranged between the above mentioned sheath connecting part 16 and optical sighting tube connecting part 23, is made of such insulating material as Teflon, is provided in the axial direction with a guide pipe hole 26 through which the above mentioned optical sighting tube guide pipe 22 is inserted and is energized to contact, for example, with the optical sighting tube connecting part 23 in the rear by a spring 28 mounted between it and a lower finger hanger 27b of finder hangers 27a and 27b provided to project above and below the above mentioned sheath connecting part 16. By the way, the above mentioned spring 28 is a plate spring in the illustrated example but may be a coil spring through two links or may be a coil spring provided between the sheath connecting part 16 and slider 25. A finger hanging ring 29 is provided below the rear of the above mentioned slider 25.

In this embodiment, on the front side of the side part of the above mentioned slider 25, an opening is made on one side surface and front surface of the above mentioned slider 25 below the above mentioned guide pipe hole 26 to form an electrode fixing groove 31 in which the above mentioned electrode device 5 is to be pressed and removably fixed. In the above mentioned sheath connecting part 16, an electrode inserting groove 32 through which the above mentioned electrode device 5 is to be inserted and further in which the above mentioned rubber packing 6 is to be pressed is formed axially through the sheath connecting part 16 from the side of the above mentioned sheath connecting part 16 to below the above mentioned optical sighting tube guide pipe 22. By the way, the above mentioned electrode fixing groove 31 and electrode inserting groove 32 open on the same side.

The above mentioned optical sighting tube 4 comprises an insertable part 21, a body part 34 connected to this insertable part 21 in the rear, a light guide connector 35 provided on the side part of this body part 34 and an eyepiece 36 connected to the above mentioned body part 34 at the rear end. Within this optical sighting tube 4, there are arranged a light guide fiber bundle not illustrated leading an illuminating light from the above mentioned light guide connector 35 to the tip of the insertable part and an image transmitting optical system not illustrated transmitting an observed image formed by an objective optical system not illustrated provided in the tip part of the above mentioned insertable part 21 to the above mentioned eyepiece 36.

Figure 4:
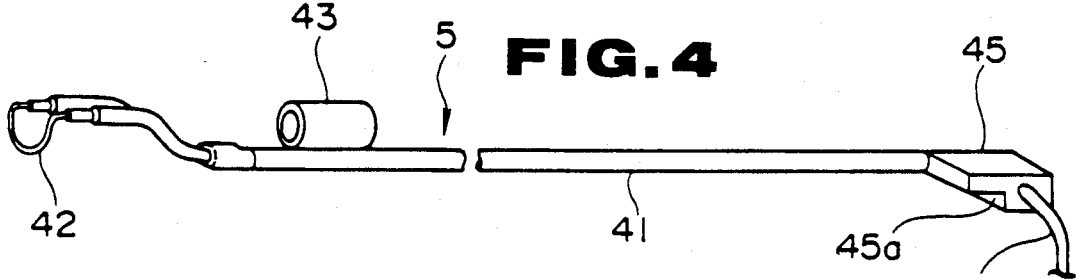
Figure 5:
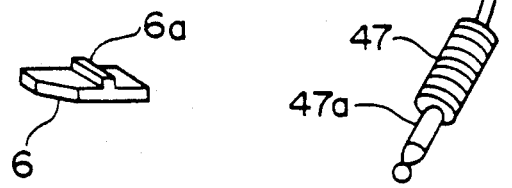

Also, as shown in FIG. 4, the above mentioned electrode device 5 has a shaft part 41 inserted through the above mentioned sheath 2, has the shaft part 41 branched to be forked on the tip side and is provided at the tips of the branches with a resecting tip electrode 42, for example, like a loop. By passing a high frequency current through the tip electrode 42, the affected part (such as the prostate gland) can be resected or incised or bleeding can be stopped. For example, a cylindrical stabilizer 43 through which the insertable part 21 of the optical sighting tube 4 is insertable is fitted to the upper part in the course of the above mentioned shaft part 41. A connector 45 to be pressed into the electrode fixing groove 31 of the above mentioned slider 25 is connected to the above mentioned shaft part 41 at the rear end. An electric cord 46 as an electric connecting means is connected to this connector 45 on the side and is provided at the tip with a connector 47 to be connected to a high frequency current source not illustrated. An electric cable not illustrated connected to the above mentioned tip electrode 42 is inserted through the above mentioned shaft part 41 and is electrically connected at the rear end with the above mentioned cord 46 within the above mentioned connector 45. By the way, the above mentioned connector 45 is made in the outside part of such insulating material as Teflon and is electrically insulated inside from outside. The electrode device 5 is electrically insulated from outside except at the tip electrode 42 and connector 47 inserting end 47a. When the above mentioned connector 47 is connected to a high frequency current source not illustrated, a high frequency current will be passed through the above mentioned tip electrode 42.

Now, the electrode fixing groove 31 formed in the above mentioned slider 25 is formed to be substantially a rectangular parallelepiped opening on the side surface and front surface of the slider 25, is made deep on the rear side and has a step 31a formed between the front side and rear side. The above mentioned connector 45 is formed to be of a shape corresponding to the above mentioned electrode fixing groove 31, that is, to be substantially a rectangular parallelepiped projecting downward on the rear side of the bottom and has a step 45a formed between the forward side and rearward side. The above mentioned connector 45 is to be pressed into the above mentioned electrode fixing groove 31 through the side opening. By the engagement of the step 45a of the connector 45 with the step 31a of the above mentioned electrode fixing groove 31, the connector 45 will be prevented from being pulled forward out of the electrode fixing groove 31. A guide groove 32a is formed in the direction intersecting at right angles with the axial direction in the central upper part in the axial direction of the electrode inserting groove 32 formed in the above mentioned sheath connecting part 16. The shaft part 41 of the above mentioned electrode device 5 is inserted into the above mentioned electrode inserting groove 32 through the side opening and then the above mentioned rubber pack 6 is pressed into the same groove 32. The rubber packing 6 is formed to be of a shape filling the above mentioned electrode inserting groove 32 when the above mentioned shaft part 41 is inserted. That is to say, the rubber packing 6 is formed to be substantially plate-like, to be concave on the inside end surface so as to closely contact the above mentioned shaft part 41 and to be continuous on the outside end surface with the outer peripheral surface of the above mentioned sheath connecting part 16 when pressed into the above mentioned electrode inserting groove 32 so as to be in close contact with the inner peripheral surface of the sheath 2 fitting part 17 and to be kept water-tight. A rib 6a corresponding to the above mentioned guide groove 32a is formed on the upper part of the rubber packing 6 so that, by the engagement of the rib 6a with the above mentioned guide groove 32a, the rubber packing 6 may be prevented from moving forward and rearward.

The operation of this embodiment formed as in the above shall be explained in the following.

The resectoscope 1 of this embodiment is assembled as in the following. First of all, the insertable part 2 of the optical sighting tube 4 is inserted into the optical sighting tube guide pipe 22 of the handle 3 and the above mentioned optical sighting tube 4 is connected to the handle 3 by the optical sighting tube connecting part 23. Then, the insertable part 21 of the above mentioned optical sighting tube 4 is inserted through the stabilizer 43 of the electrode device 5, then the shaft part 41 of the above mentioned electrode device 5 is inserted from the side into the electrode inserting groove 32 of the sheath connecting part 16 and further the connector 45 is pressed from the side into the electrode fixing groove 31 to fit the electrode device 5 to the handle 3. Then, the rubber packing 6 is pressed into the electrode inserting groove 32 in which the shaft part 41 of the above mentioned electrode device 5 has been inserted. The part before the sheath connecting part 16 of the handle 3 to which the optical sighting tube 4 and electrode device 5 are assembled is inserted into the sheath 2 and the above mentioned sheath connecting part 16 is fitted into the sheath 2 fitting part 17. The electrode 5 connector 47 is connected to a high frequency current source not illustrated. A light guide cable connected to a light source apparatus not illustrated is connected to the light guide connector 35 of the optical sighting tube 4.

In the thus assembled resectoscope 1, the slider 25 is moved forward and rearward by the operation of fingers holding finger hangers 27a and 27b and a finger hanging ring 29 of the handle 3 so that the electrode device 5 mechanically connected to the above mentioned slider 25 by the connecting part 45 may be moved forward and rearward and the tip electrode 42 may be projected and retracted from the sheath 2 tip.

The high frequency current from the high frequency current source is transmitted to the above mentioned tip electrode 42 through the electric cable within the electric cord 46 and shaft part 41 so that the affected part (such as the prostate gland) may be resected or incised or bleeding may be stopped by this tip electrode 42.

In this embodiment, the electrode device 5 is electrically insulated from outside except at the tip electrode 42 and the inserting end 47a of the connector 47. Therefore, the high frequency current is transmitted to the tip electrode 42 through the electric cord 46, connector 45 and shaft part 41 perfectly insulated from outside without passing through such electric connecting part not insulated within the slider 25 as in the past, therefore the electric leak can be prevented and the electric safety can be improved.

As there is no electric connecting mechanism within the slider 25, no contact will fail and a stabilized high frequency output will be obtained.

Further, as there is no electric connecting mechanism within the slider 25, the electrode device 5 removably fitting mechanism can be simply pressed into the electrode fixing groove 31, the slider 25 can be made small and light and therefore the fatigue in the operation can be reduced.

There is no operating part for removably fitting the electrode device to the slider 25. Even if a dirt or blood is deposited on the slider 25, it will be simply swept, the removably fitting mechanism will neither fail in the operation nor cause a trouble.

Figure 6:
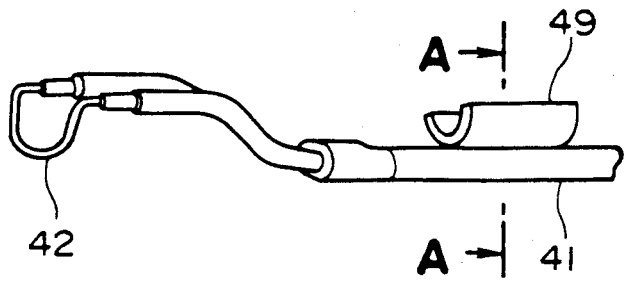
Figure 7:

A modification of the first embodiment is shown in FIGS. 6 and 7.

In this modification, the shape of a stabilizer 49 fitted to the shaft part 41 of the electrode device 5 is made semi-cylindrical with a semi-circular cross-section in the axial direction and, as shown in FIG. 7, the opening in the diametral direction of this stabilizer 49 is arranged upward as inclined somewhat sidewise so that the insertable part 21 of the optical sighting tube 4 may be inserted from the side into the above mentioned stabilizer 49 in fitting the electrode device 5 to the handle 3. The other formations are the same as in the first embodiment.

According to this modification, in fitting the electrode device 5 to the handle 3, the insertable part 21 of the optical sighting tube 4 can be inserted from the side into the stabilizer 49, therefore it is not necessary to insert the insertable part 21 of the optical sighting tube 4 first into the stabilizer and the fitting is easy and can be made without bending the shaft part 41.

Figure 8:
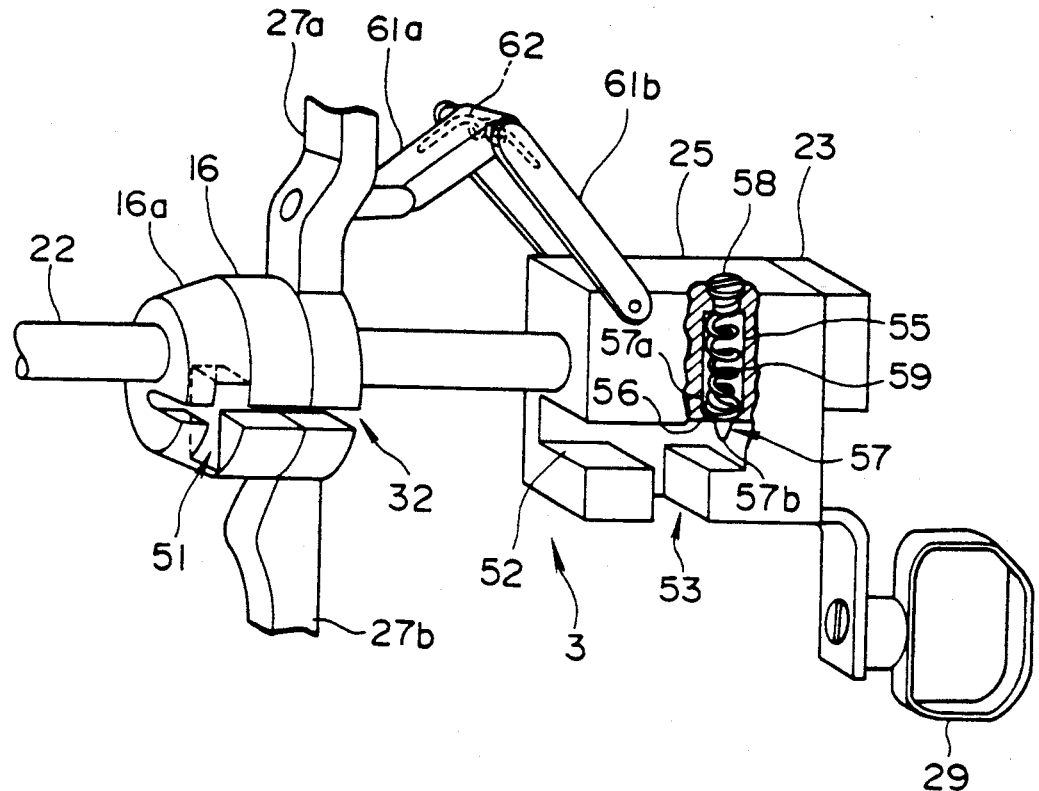
FIGS. 8 and 9 relate to the second embodiment of the present invention.
Figure 9:
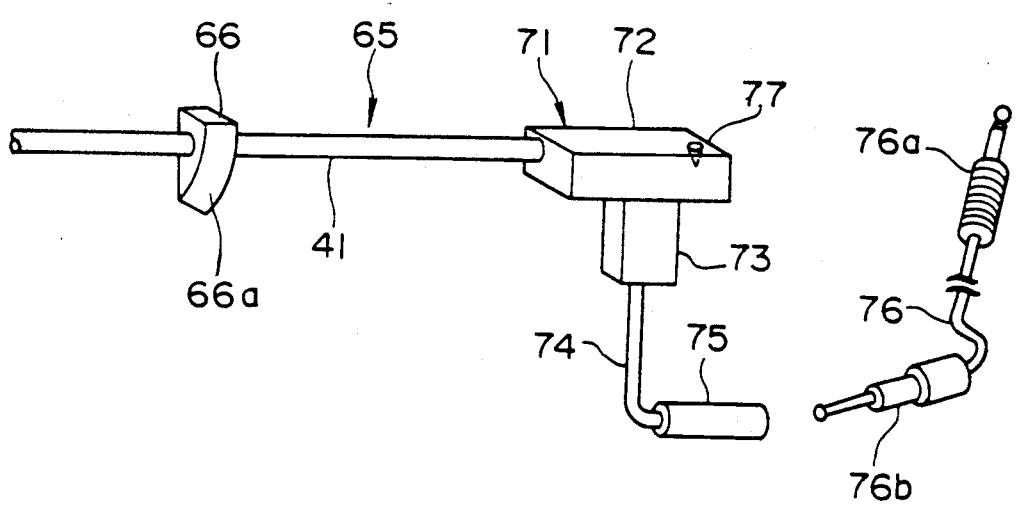

The second embodiment of the present invention is shown in FIGS. 8 and 9.

In this embodiment, as shown in FIG. 8, the same as in the first embodiment, an electrode inserting groove 32 is formed forward and rearward through a sheath connecting part 16 from the side of the sheath connecting part 16 to the lower side of an optical sighting tube guide tube 22. A packing groove 51 having a substantially sector-shaped cross-section in the axial direction and opening on the same side as of the opening of the above mentioned electrode inserting groove 32 is formed so to intersect in the vertical direction with the above mentioned electrode inserting groove 32 from a tapered surface 16 of a small diameter on the tip side formed on the tip side of the above mentioned sheath connecting part 16 to the inside in the diametral direction.

In a slider 25, an electrode fixing groove 52 formed to be a rectangular parallelepiped opening on one side and front surface is formed and a vertical groove 53 opening on the side surface and bottom surface of the slider 25 from the bottom surface of this electrode fixing groove 52 to the bottom surface of the slider 25 is formed. A clicking hole 55 is formed from the upper surface of the slider 25 to the above mentioned electrode fixing groove 52, has an engaging part 56 of a small diameter at the end on the above mentioned electrode fixing groove 52 side and has a female screw formed on the end side on the upper surface side of the slider 25. A clicking pin 57 consisting of a stopper part 57a of a diameter larger than of the above mentioned engaging part and a pin part 57b connected to this stopper part 57a and having a diameter smaller than of the above mentioned engaging part 56 is arranged in this clicking hole 55 so as to project on the above mentioned electrode fixing groove 52 side by a predetermined amount of the above mentioned pin part 57b. A screw 58 is screwed to the female screw of the above mentioned clicking hole 55. A clicking spring 59 energizing the above mentioned clicking pin 57 to the electrode fixing groove 52 side is provided between this screw 58 and the stopper part 57a of the above mentioned clicking pin 57.

In this embodiment, instead of the spring 28 in the first embodiment, links 61a and 61b are mounted between an upper finger hanger 27a and the slider 25. A coil spring 62 energizing these links 61a and 61b, for example, in the opening direction is fitted to the connecting part of the above mentioned links 61a and 61b so that the above mentioned slider 25 may be energized by this coil spring 62, for example, to the optical sighting tube connecting part 23 side.

On the other hand, as shown in FIG. 9, a packing 66 to be pressed into a packing hole 51 formed in the above mentioned sheath connecting part 16 is slidably fitted to the shaft part 41 of the electrode device 65, is formed to be of a substantially sector-like cross-section corresponding to the above mentioned packing hole 51 and is formed on the outer peripheral surface 66a to continue with the tapered surface 16a of the above mentioned sheath connecting part 16 when pressed into the above mentioned packing groove 51 so as to keep the watertightness in close contact with the inner peripheral surface of the sheath 2 fitting part 17.

A connector 71 connected to the above mentioned shaft part 41 has a rectangular parallelepipedal body 72 corresponding to the above mentioned electrode fixing groove 52 and a rectangular parallelepipedal lower body 73 provided to project below this body 7 and insertable into the above mentioned vertical groove 53. An electric cord 74 electrically connected to the tip electrode 42 is connected to the above mentioned lower body 73 at the lower end and is provided at the end with a connector 75 to be connected with a plug 76b of an electric connecting cord 76 having a connector 76a to be connected to a high frequency current source and the above mentioned plug 76b to be connected to the above mentioned connector 75 at the respective ends. The above mentioned electrode device 65 is to be connected with the high frequency current source through the above mentioned electric connecting cord 76.

A conical hole 77 with which the pin part 57b of the above mentioned clicking pin 57 is to be engaged is provided in the position corresponding to this clicking pin 57 on the upper surface of the above mentioned body 72.

The other formations are the same as in the first embodiment

In this embodiment, in fixing the electrode device 65 to the handle 3, the shaft part 41 of the electrode device 65 is inserted from the side into the electrode inserting groove 32 of the sheath connecting part 16 and the packing 66 slidably fitted to this shaft part 41 is pressed into the packing hole 51. The connector 71 is inserted from the side into the above mentioned electrode fixing groove 52 and vertical groove 53 so that the body 72 may fit in the electrode fixing groove 52 and the lower body 73 may fit the vertical groove 53. When the pin part 57b of the clicking pin 57 engages with the conical hole 77 of the above mentioned body 73, the electrode device 65 will be removably connected to the slider 25. By the engagement of the above mentioned lower body 73 with the vertical groove 53, the electrode device 65 will be fixed so as not to move forward and rearward with respect to the slider 25.

According to this embodiment, the electrode device 65 can be positively fixed by the clicking pin 57 and the packing 66 is slidably fitted to the shaft part 41 of the electrode device 65 and is not likely to be lost.

Also, as the electric cord 74 is connected below the handle 3, even in case the handle 3 is held by a left hand, the cord 74 will not touch the hand and will not be in the way of the operation. Further, the electric cord 74 is short and can be separated from the electric connecting cord 76 near the connector 71 and therefore the connector device 65 is easy to fit and remove.

The other operations and effects are the same as in the first embodiment.

Figure 10:
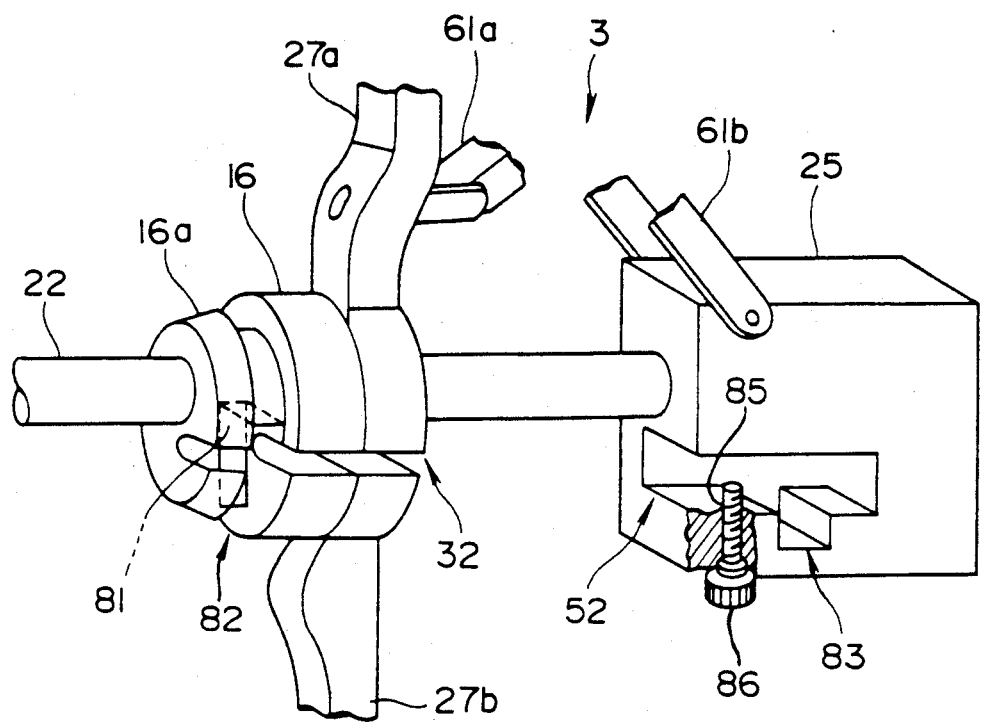
FIGS. 10 to 12 relate to the third embodiment of the present invention.
Figure 11:
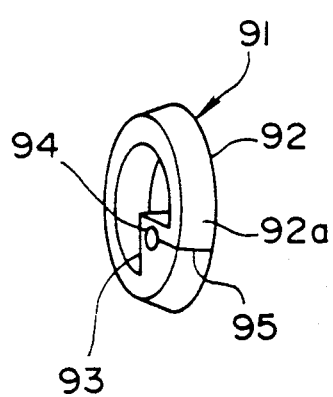
Figure 12:
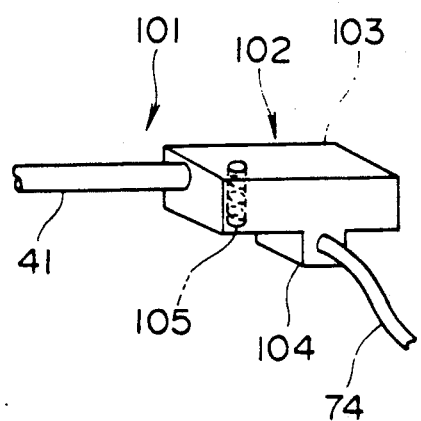

The third embodiment of the present invention is shown in FIGS. 10 to 12.

In this embodiment, as shown in FIG. 10, the same as in the second embodiment, a vertical groove 81 substantially sector-like in the cross-section in the axial direction is formed so as to intersect in the vertical direction with the electrode inserting groove 32 and a peripheral groove 82 continuing to the above mentioned vertical groove 81 and opening on the tapered surface 16a of the above mentioned sheath connecting part 16 is formed in the same position in the axial direction as of this vertical groove 81.

An electrode fixing groove 52 formed to be a rectangular parallelepiped opening on one side surface and front surface is formed in this slider 25 and a guide groove 83 opening on the side of the slider 25 is formed in the direction intersecting substantially at right angles with the axial direction on the bottom surface of this electrode fixing groove 52. A screw hole 85 is formed through the bottom surface of the above mentioned electrode fixing groove 52 from the bottom surface of the above mentioned slider 25 and a screw 86 longer than this screw hole 85 is screwed into the above mentioned screw hole 85.

On the other hand, as shown in FIG. 11, a packing 91 to be pressed into the vertical groove 81 and peripheral groove 82 of the above mentioned sheath connecting part 16 has an annular part 92 filling the entire periphery of the above mentioned peripheral groove 82 and an internal projection 93 of a substantially sector-like cross-section in the axial direction formed inside this annular part 92 and filling the above mentioned vertical groove 81. The outer peripheral surface 92a of the above mentioned annular part 92 is formed to continue with the tapered surface 16a of the above mentioned sheath connecting part 16 when pressed into the above mentioned peripheral groove 82 so as to keep the water-tightness in close contact with the inner peripheral surface of the fitting part 17 of the sheath 2. A shaft hole 94 to be slidably fitted to the shaft part 41 of the electrode device 101 is formed in the above mentioned projection 93 and further a slit 95 is formed from the outer peripheral surface 92a of the above mentioned annular part 92 to the above mentioned shaft hole 94 so that the above mentioned shaft part 41 may be inserted into the above mentioned shaft hole 94.

Also, the connector 102 connected to the above mentioned shaft part 41 at the rear end has a rectangular parallelepipedal body 103 corresponding to the above mentioned electrode fixing groove 52 and a rectangular parallelepipedal rib 104 projected below this body 103 and insertable into the above mentioned guide groove 83. An electric cord 74 electrically connected to the tip electrode 42 is connected to the side of the above mentioned rib 104. A screw hole 105 into which the above mentioned screw 86 is to be screwed is formed in the bottom of the above mentioned body 103.

The other formations are the same as in the first and second embodiments.

In this embodiment, when the packing 91 has been annularly fitted in the vertical groove 81 and peripheral groove 82 of the sheath connecting part 16, the shaft part 41 of the electrode device 101 is inserted into the shaft hole 94 through the slit 95. The connector 102 is inserted form the side of the slider 25 into the electrode fixing groove 52 and guide groove 83 and has the screw 86 screwed into the screw hole 105 so as to be fixed to the slider 25.

According to this embodiment, the electrode device 102 is fixed by the screw 86 and therefore is not likely to be accidentally removed.

The other operations and effects are the same as in the first and second embodiments.

Figure 13:
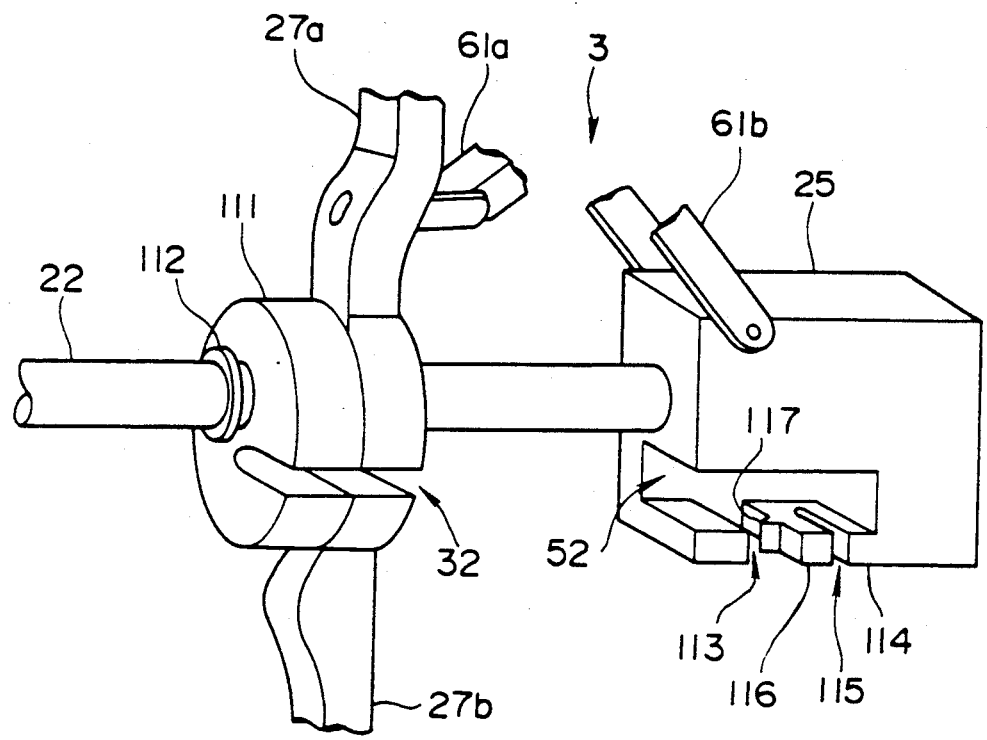
FIGS. 13 and 14 relate to the fourth embodiment of the present invention.
Figure 14:
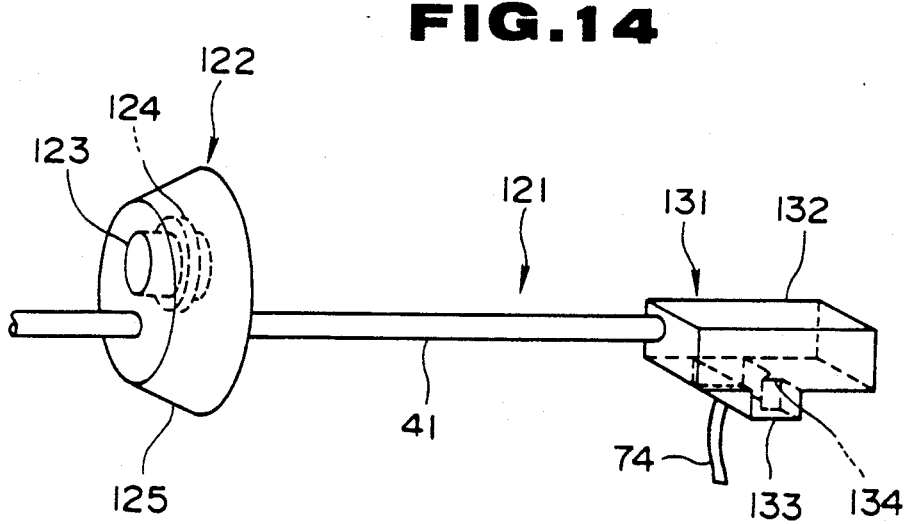

The fourth embodiment of the present invention is shown in FIGS. 13 and 14.

In this embodiment, as shown in FIG. 13, an electrode inserting hole 32 is formed in a sheath connecting part 111 and a projecting ring 112 is formed on the outer periphery of an optical sighting tube guide tube 22 forward of this sheath connecting part 111.

In the slider 25, there are formed an electrode fixing groove 52 formed to be a rectangular parallelepiped opening on one side surface and front surface and a guide groove 113 opening on the side surface of the slider 25 from the substantially central part in the axial direction of the bottom surface of this electrode fixing groove 52 to the bottom surface of the slider 25.

Further, on one of the floors of the electrode fixing groove 52 divided in the front and rear by the above mentioned guide groove 113, for example, on the rear floor 114, a slit 115 is formed in the same direction as of the above mentioned guide groove 113 and a beam 116 is formed between the above mentioned guide groove 113 and slit 115. A triangular projection 117 is formed on the side surface on the guide groove 113 side of this beam 116.

On the other hand, as shown in FIG. 14, a packing 122 is slidably fitted to a shaft part 41 of an electrode device 121 and is to be connected to the above mentioned sheath connecting part 111 at the front end. A hole 123 through which an optical sighting tube guide tube 22 is to be inserted is formed in the axial direction through this packing 122. An annular groove 124 fitting the above mentioned projecting ring 112 is formed in the position corresponding to this projecting ring 112 within this hole 123. The outer peripheral surface of the above mentioned packing 122 is formed to be a tapered surface 125 which is to keep the water-tightness in close contact with the inner peripheral surface of the sheath 2 fitting part 17.

A connector 131 connected to the above mentioned shaft part 141 at the rear end has a rectangular parallelepipedal body 132 corresponding to the above mentioned electrode fixing groove 52 and a rectangular parallelepipedal rib 133 projected below this body 132 and insertable into the above mentioned guide groove 113. An electric cord 74 electrically connected to a tip electrode 42 is connected to the above mentioned rib 133 in the bottom.

A triangular groove 134 fitting the above mentioned triangular projection 117 is formed in the position corresponding to this triangular projection 117.

The other formations are the same as in the first and second embodiments.

In this embodiment, the optical sighting tube guide pipe 22 is inserted through the hole 123 of the packing 122 and the projecting ring 112 is fitted in the annular groove 124 so that this packing 122 may be connected forward of the sheath connecting part 111 and the tapered surface 125 of the above mentioned packing 122 may be in close contact with the inner peripheral surface of the sheath 2 fitting part 17 to keep the watertightness.

At the same time, the shaft part 41 of the electrode device 121 is inserted into the electrode inserting groove 32 and the connector 131 is inserted into the electrode fixing groove 52 and guide groove 113 of the slider 25 until the triangular projection 117 fits in the triangular groove 135 so that the resiliency of the beam 116 may alway energize the above mentioned triangular projection 117 to the triangular groove 134 side and the connector 131 may be fixed to the slider 25.

According to this embodiment, the electrode device 121 fixing mechanism of the slider 25 is simpler and the simple and easy handle 3 unlikely to fail can be provided.

The other operations and effects are the same as in the first and second embodiments.

The fifth embodiment of the present invention is shown in FIG. 15.

In this embodiment, a slider 301 is provided with an electrode inserting hole 302 consisting of a straight hole 302a formed in the axial direction rearward from the front end surface and an arcuate hole 302b formed from the rear end of this hole 302a to the lower end surface of the slider 301 as connected with the above mentioned hole 302a. A sheath connecting part 16 is provided with an electrode inserting hole 201 the same as in the fifth embodiment.

An electrode device 310 in this embodiment if formed of a rigid straight shaft part 312 and a cord part 313 which is a flexible electric cord connected to this shaft part 312 at the rear end. The above mentioned shaft part 312 is forked at the tip the same as in the first embodiment and is provided at the tip with the same loop-like resecting tip electrode 42 as in the first embodiment. On the other hand, the above mentioned cord part 313 is provided at the rear end with an electric connector 315 which is electrically connected with the above mentioned resecting tip electrode 42 by an electric cable 216 inserted through the electrode driving shaft 311. An electric connector 317 of an electric cord 316 connected to a high frequency current source not illustrated is to be connected to the above mentioned electric connector 315.

The above mentioned electrode device 310 is inserted from the cord part 313 through the electrode inserting hole 201 of the sheath connecting part 16 and the electrode inserting hole 302 of the slider 301, is inserted at the rear end of the shaft part 312 through the straight hole 302a of the above mentioned electrode inserting hole 302, is inserted in the cord part 313 through the accurate hole 302b of the above mentioned electrode inserting hole 302 and is led at the rear end of this cord part 313 out of the lower end surface of the slider 301.

A screw hole communicating with the straight hole 302a of the above mentioned electrode inserting hole 302 is formed, for example, on the side of the above mentioned slider 301 and a screw 318 fixing the shaft part 312 of the electrode device 310 inserted through the above mentioned hole 302a is screwed into this screw hole.

In this embodiment, the electrode device 310 is inserted through the electrode inserting hole 201 of the sheath connecting part 16 and the electrode inserting hole 302 of the slider 301 and is fixed in the shaft part 312 to the slider 301 by the screw 318. The electric connector 315 at the rear end of the cord part 313 is connected with the electric cord 316.

According to this embodiment, as the entire electrode device 310 is replaceable from the front surface of the sheath connecting part 16, the sheath connecting part 16 need not be incised on the side, no water-tight structure by a special packing or the like is required and water is not likely to leak.

The other operations and effects are the same as in the first embodiment.

The sixth embodiment of the present invention is shown in FIG. 16.

In a resectoscope 200 of this embodiment, an electrode inserting hole 201 passing in the axial direction is formed below an optical sighting tube guide pipe 22 in a sheath connecting part 16 of a handle 3.

An electrode device 210 of this embodiment comprises an electrode driving shaft 211 slidably inserted through the above mentioned electrode inserting hole 201 and fixed at the rear end to a slider 202 of the above mentioned handle 3, an electrode part 212 removably connected to this electrode driving shaft 211 at the tip, an electric cord 213 extended from the above mentioned slider 202, for example, in the bottom and a connector 214 provided at the tip of this electric cord 213 and connected to a high frequency current source not illustrated. The above mentioned electrode driving shaft 211 is formed of an insulating material in the outside part and has an electric cable 216 inserted through it and connected with the above mentioned electric cord 213. The above mentioned slider 202 is of a watertight structure and has the electric connecting part of the electric cable 216 and electric cord 213 within this slider 202 insulated from outside.

The above mentioned electrode driving shaft 211 is provided within the tip part with an electric connector 218 connected to the above mentioned electric cable 216 and below the outer peripheral part with an electrode fixing pin 219 and is further fitted above the outer peripheral part, for example, with a cylindrical stabilizer 220 through which the optical sighting tube guide tube 22 is inserted.

On the other hand, the above mentioned electrode part 212 comprises an electrode body 222 having, for example, a hook-like tip electrode 221 on the tip side, an electric connector 223 provided at the rear end of the electrode body 222 and electrically connected to the above mentioned tip electrode 221, a rotatable electrode fixing device 224 connected to the above mentioned electrode body 222 on the lower side and having a hole in which the above mentioned electrode fixing pin 219 is to be inserted and, for example, a cylindrical stabilizer 226 which is fitted on the upper side of the above mentioned electrode body 220 and through which the above mentioned optical sighting tube guide pipe 22 is to be inserted. The above mentioned electrode body 222 and electrode fixing device 224 may be integrally formed, for example, of polypropylens so that their jointing part may be repeatedly bent.

In the above mentioned electrode part 212, the optical sighting tube guide pipe 22 is inserted through the stabilizer 226, the electric connectors 223 and 218 are connected with each other and the hole 225 of the electrode fixing device 224 is fitted to the electrode fixing pin 219 so that the electrode part 212 may be electrically and mechanically connected to the above mentioned electrode driving shaft 211.

By the way, in case the above mentioned electric connectors 218 and 223 are connected with each other within the electrode driving shaft 211 and the electrode part 212 and electrode driving shaft 211 are connected with each other, the interior of the electrode driving shaft 211 will be kept water-tight so that the electric connecting part of the above mentioned electric connectors 218 and 223 may be insulated from outside.

Also, the inner peripheral surface of the sheath 2 not illustrated in FIG. 15 is formed of an insulating material.

The other formations are the same as in the first embodiment.

The resectoscope 200 of this embodiment is assembled as in the following. That is to say, the optical sighting tube 4 is connected to the handle 3 and the electrode part 212 is connected to the tip part of the electrode driving shaft 211. The handle 3 to which the optical sighting tube 4 and electrode part 212 have been thus assembled is connected to the sheath 2. The connector 214 provided at the tip of the electric cord 213 is connected to a high frequency current source not illustrated. The light guide cable connected to the light source apparatus not illustrated is connected to the light guide connector 35 of the optical sighting tube 4.

In the thus assembled resectoscope 200, when the slider 202 is moved forward and rearward by the operation of fingers holding the finger hangers 27a and 27b and finger hanging ring 29, the electrode driving shaft 211 connected and fixed to this slider 202 will move forward and rearward and the tip electrode 221 of the electrode part 212 connected to this electrode driving shaft 211 will be projected and retracted from the sheath 2 tip.

The high frequency current from the high frequency current source will be transmitted to the above mentioned tip electrode 221 through the electric cord 213, electric cable 216 within the electrode driving shaft 211 and electric connectors 218 and 223 and the affected part (such as the prostate gland) will be able to be resected or incised or the bleeding part will be able to be stopped.

In the electrode device 210 in this embodiment, the electrode part 212 and electrode driving shaft 211 are electrically connected with each other in the tip side part of the handle 3 to be inserted into the sheath 2. The others than this electric connecting part are electrically insulated from outside and this electric connecting part will be also insulated from outside when connected. Such members around the electric connecting part of this electrode part 212 and electrode driving shaft 211 as the electrode driving shaft 211 and sheath 2 are formed on the inner surfaces of an insulating material. Therefore, the high frequency current will be transmitted to the tip electrode 221 through the cord 213, electric cable 216 within the electrode driving shaft 211 and electric connectors 218 and 223 insulated from outside without passing through an electric connecting part not insulated within such slider as in the past. Therefore, the electric leak can be prevented and the electric safety will improve.

As there is no electric connecting mechanism within the slider 202, the contact will not fail and a stabilized high frequency output will be obtained.

Further, as there is no electric and mechanical connecting mechanism within the slider 202, the slider 202 can be small and light.

Further, in the electrode device 210, as the electrode driving shaft 211 is commonly used for a plurality of electrode parts 212 and the parts to be replaced, that is, the formation of the electrode part 212 will reduce, in the case of using a plurality of kinds of the electrode device 210, the cost will be able to be reduced.

By the way, in this embodiment, even in case a high frequency current leaks from the electric connecting part of the electrode part 212 and electrode driving shaft 211, as the peripheral members are formed of an insulating material, this high frequency current will flow into the irrigation and will not be likely to cause a spark or burn.

The seventh embodiment of the present invention is shown in FIG. 17.

In this embodiment, an electrode fixing pipe 232 through which an optical sighting tube guide pipe 22 is slidably inserted is fitted on the upper side of the tip part of an electrode driving shaft 231. This electrode fixing pipe 232 on the tip side is incised in the upper part to form a hook part 232a. An electric connector 233 is provided in the tip part of the above mentioned electrode driving shaft 231.

On the other hand, in an electrode part 234, tip electrode shafts 236a and 236b are fitted on the front sides of both side parts, for example, of a saddle-like stabilizer 235 and a loop-like tip electrode 237 is fitted between the tips of these tip electrode shafts 236a and 236b. Cords 238 are extended respectively from the above mentioned tip electrode shafts 236a and 236b at the rear ends and are provided at the respective ends with electric connectors 239 to be connected to the above mentioned electric connector 233. A hook part 235a to be engaged with the hook part 232a of the above mentioned electrode fixing pipe 232 is formed on the rear end side of the above mentioned stabilizer 235.

The other formations are the same as in the fifth embodiment.

In this embodiment, when the stabilizer 235 of the electrode part 234 is fitted to the optical sighting tube guide pipe 22 from above and the hook part 235a of this stabilizer 235 is engaged with the hook part 232a of the electrode fixing pipe 232, the electrode part 234 and electrode driving shaft 231 will be mechanically connected with each other. When the electric connector 239 of the electrode part 234 and the electric connector 233 of the electrode driving shaft 231 are connected with each other, the electrode part 234 and electrode driving shaft 231 will be electrically connected with each other.

The other operations and effects are the same as in the fifth embodiment.

Figure 18:
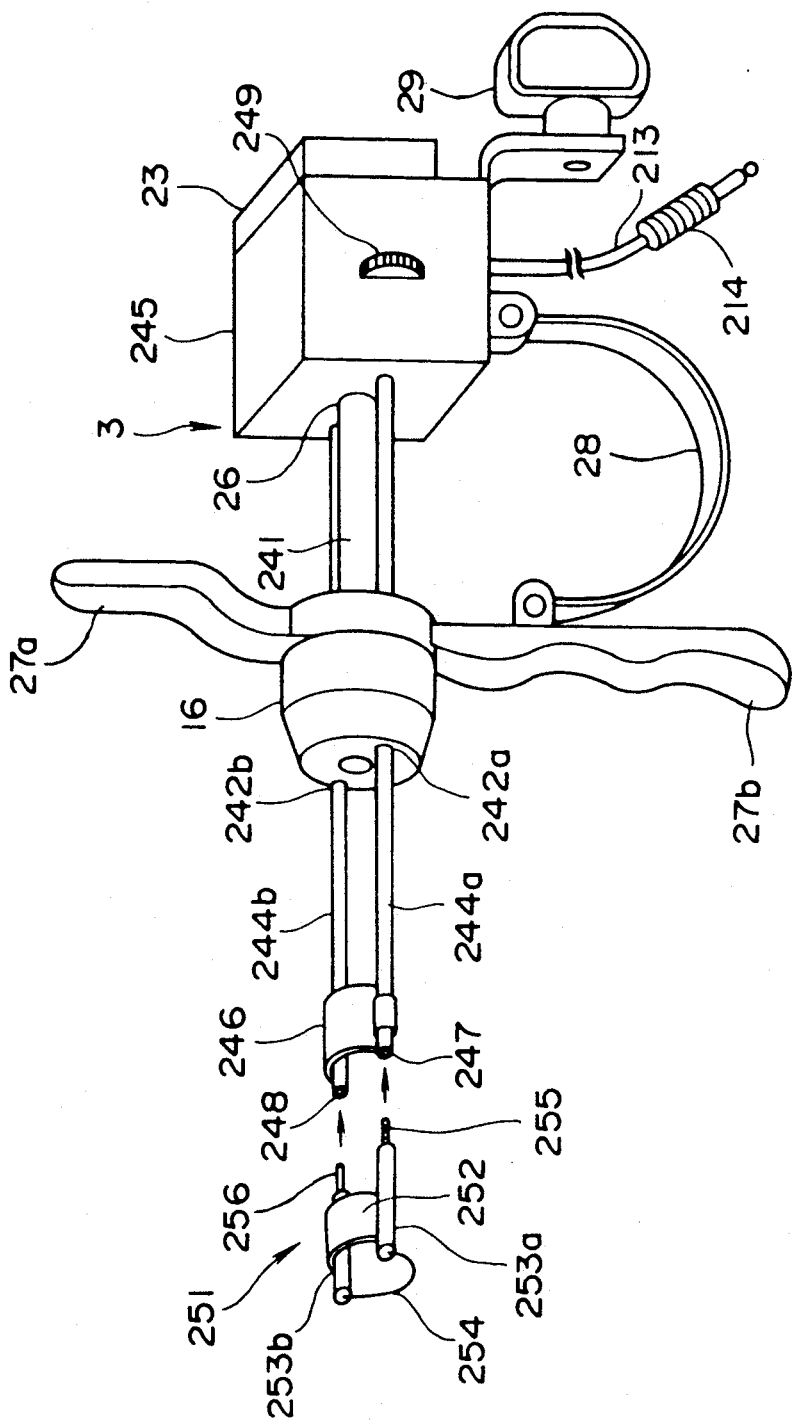
FIG. 18 is a perspective view showing a handle and electrode device in the eighth embodiment of the present invention.

The eighth embodiment of the present invention is shown in FIG. 18.

In this embodiment, an optical sighting tube guide pipe 241 is mounted forward and rearward through substantially the central part of a sheath connecting part 16 of a handle 3 from this sheath connecting part 16 to an optical sighting tube connecting part 23. Forward and rearward passing electrode inserting holes 242a and 242b are provided on both sides of the above mentioned optical sighting tube guide pipe 241 of the above mentioned sheath connecting part 16. Electrode fitting shafts 244a and 244b are slidably inserted respectively through the electrode inserting holes 242a and 242b, are connected at the rear ends to a slider 245 provided between the above mentioned sheath connecting part 16 and optical sighting tube connecting part 23 and are supported on the tip sides by a semi-cylindrical stabilizer 246 so that one electrode fitting shaft 244a may be rotatable. A female screw 247 is formed at the tip of one electrode fitting shaft 244a. An electric connector 248 is provided at the tip of the other electrode fitting shaft 244b and is connected to an electric cord 213 through an electric cable not illustrated inserted through the electrode driving shaft 244b. A rotary grip 249 is provided on the side of the above mentioned slider 245 so that, by rotating this rotary grip 249, one electrode fitting shaft 244a may be rotated through a power transmitting mechanism not illustrated within the slider 245.

On the other hand, the electrode part 251 is fitted with tip electrode shafts 253a and 253b on both sides, for example, of a semi-cylindrical stabilizer 252 and has a loop-like tip electrode 254 fitted between the tips of these tip electrode shafts 253a and 253b. A male screw 255 to be screwed in the above mentioned female screw 247 is formed at the rear end of one tip electrode shaft 253a. An electric connector 256 connected to the above mentioned tip electrode 254 and to the above mentioned electric connector 248 is provided at the rear end of the other tip electrode shaft 253b.

In this embodiment, when the male screw 255 of the electrode part 251 is inserted into the female screw 247 of the electrode fitting shaft 244a and the rotary grip 249 of the slider 245 is rotated to rotate the above mentioned electrode fitting shaft 244a, the above mentioned male screw 255 and female screw 247 will be screwed with each other and the electrode part 251 will be mechanically connected with the electrode fitting shaft 244a. At the same time, when the electric connector 256 of the electrode part 251 is connected with the electric connector 248 of the electrode fitting shaft 244b, the electrode fitting shaft 244b, the electrode part 251 will be connected to the electric cord 213 through the electric cable within the electrode fitting shaft 244b.

The other operations and effects are the same as in the sixth embodiment.

Figure 19:
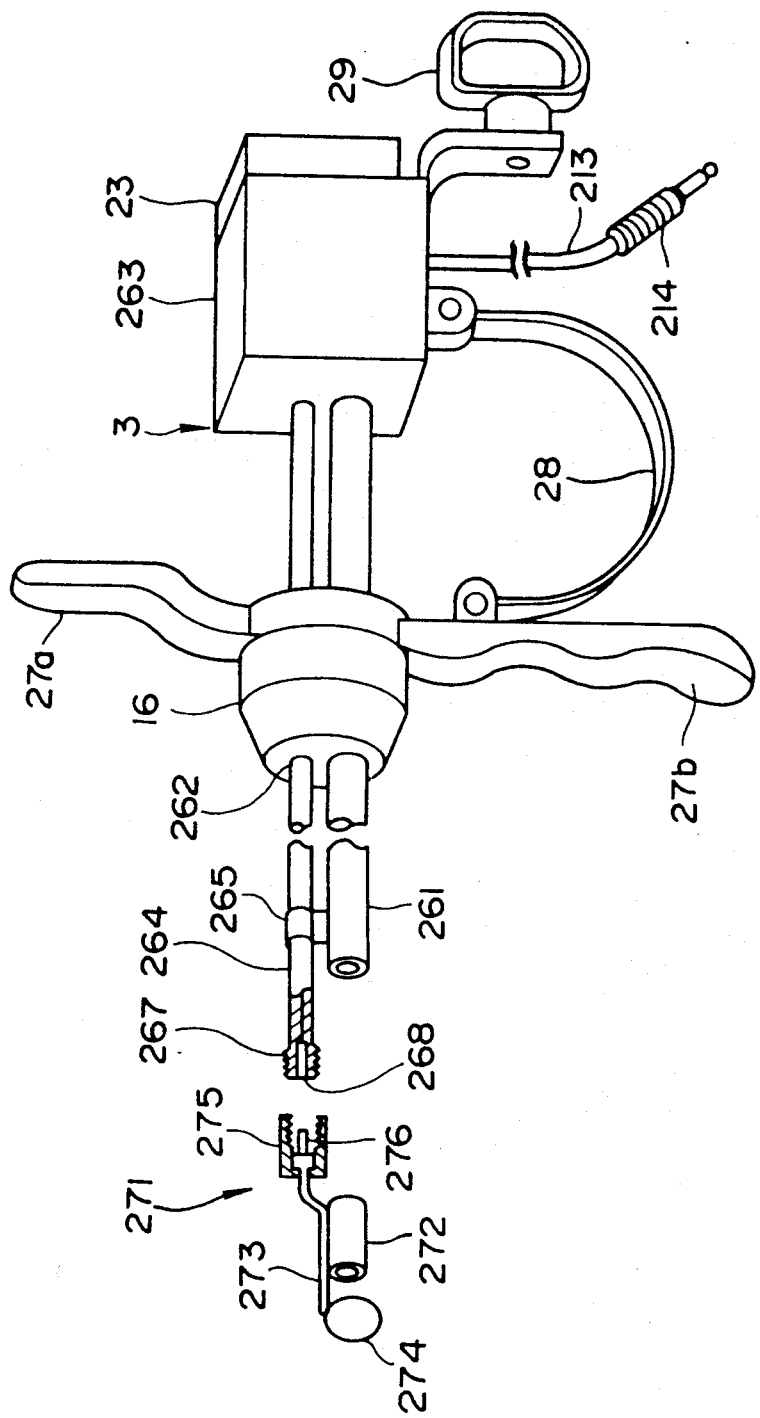
FIG. 19 is a partly sectioned perspective view showing a handle and electrode device in the ninth embodiment of the present invention.

The ninth embodiment of the present invention is shown in FIG. 19.

In this embodiment, an optical sighting tube guide pipe 261 is on the lower side of a sheath connecting part 16 and an electrode inserting hole 262 passing forward and rearward through the above mentioned sheath connecting part 16 is provided on the upper side of this optical sighting tube guide pipe 261. An electrode driving shaft 264 connected and fixed at the rear end to a slider 263 is inserted through this electrode inserting hole 262 is inserted on the tip side through a stabilizer 265 fitted above the above mentioned optical sighting tube guide pipe 261, has a male screw 267 formed on the outer periphery in the tip part and is provided inside with an electric connector 268.

On the other hand, an electrode part 271 is fitted with a tip electrode shaft 273 in the upper part of a stabilizer 272 through which an insertable part of a optical sighting tube not illustrated is to be inserted and is fitted with a loop-like tip electrode 274 at the tip of this tip electrode shaft 273 fitted at the rear end rotatably with a female screw 275 to be screwed with the above mentioned male screw 267. An electric connector 276 to be connected with the above mentioned tip electrode 274 and with the above mentioned electric connector 268 is provided within this female screw 275.

The other formations are the same as in the sixth embodiment.

In this embodiment, by rotating the female screw 275 of the electrode part 271 to be screwed with the male screw 267 of the electrode driving shaft 264, the electrode part 271 is mechanically connected with the electrode driving shaft 264, the electric connectors 268 and 276 are connected with each other and the electrode part 271 is connected also electrically.

The other operations and effects are the same as in the sixth embodiment.

Figure 20:
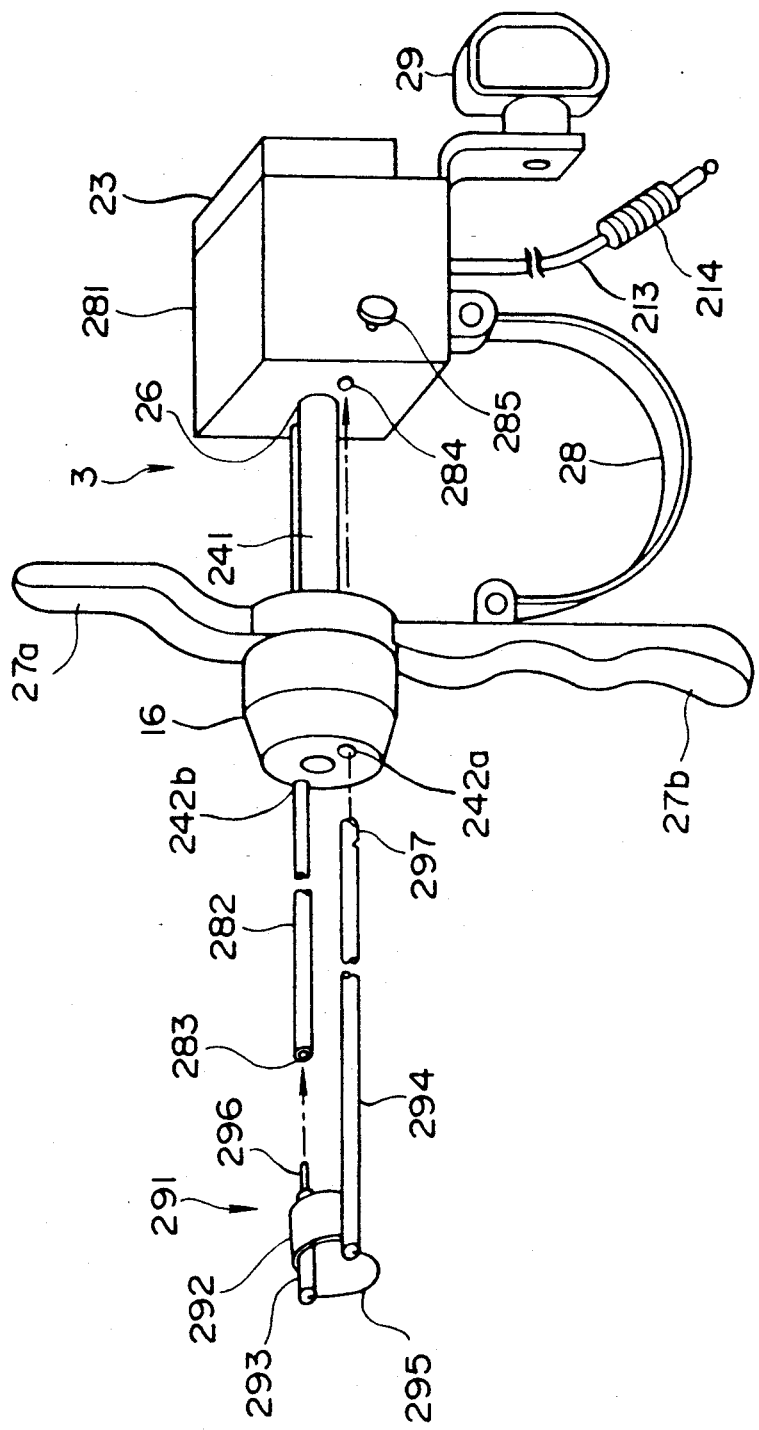
FIG. 20 is a perspective view showing a handle and electrode device in the tenth embodiment of the present invention.
Figure 28:
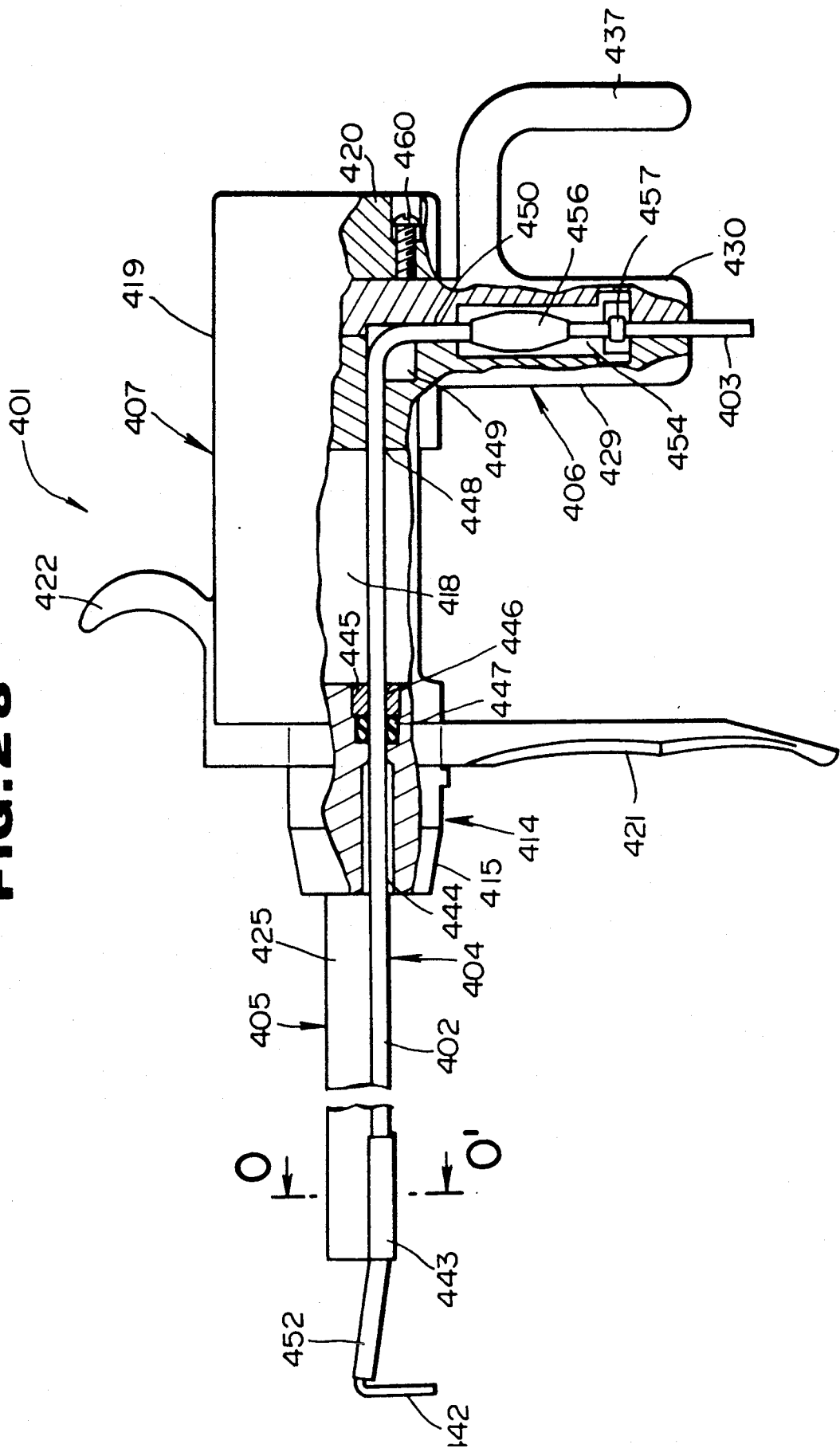

The tenth embodiment of the present invention is shown in FIG. 20.

In this embodiment, the same as in the eighth embodiment, an optical sighting tube guide pipe 241 is mounted forward and rearward through substantially the central part of a sheath connecting part 16 of a handle 3 from this sheath connecting part 16 to an optical sighting tube connecting part 23. Forward and rearward passing electrode inserting holes 242a and 242b are provided on both sides of the above mentioned optical sighting tube guide pipe 241 of the above mentioned sheath connecting part 16. An electrode fitting shaft 282 connected and fixed at the rear end to a slider 281 is slidably inserted through one electrode inserting hole 242b and is provided at the tip with an electric connector 283. An electrode inserting hole 284 is formed coaxially with the other electrode inserting hole 242a on the front surface of the above mentioned slider 281. A removably fitting button 285 removably fitting an electrode by operating a removably fitting mechanism not illustrated within the above mentioned electrode inserting hole 284 is provided on the side of the above mentioned slider 281.

On the other hand, in an electrode part 291, a short tip electrode shaft 293 is fitted to the above mentioned electrode fitting shaft 282 side, for example, of a semi-cylindrical stabilizer 292 and a long tip electrode shaft 294 is fitted to the other side. A loop-like tip electrode 295 is fitted between the tips of these tip electrode shafts 293 and 294. The above mentioned tip electrode shaft 293 is provided at the rear end with an electric connector 296 to be connected to the above mentioned electric connector 283. For example, a hook-like connecting part 297 to be inserted in the electrode inserting hole 284 of the above mentioned slider 281 and to be fixed to the slider 281 by a removably fitting mechanism not illustrated within this electrode inserting hole 284 is formed at the rear end of the above mentioned tip electrode shaft 294.

By the way, the above mentioned tip electrode shaft 294 is formed to be of such length that the above mentioned contact part 297 will be inserted and fixed in the electrode inserting hole 284 of the slider 281 when the electric connector 296 of the electrode part 291 and the electric connector 283 of the electrode fitting shaft 282 are connected with each other.

The other formations are the same as in the sixth embodiment.

In this embodiment, when the electric connector 296 of the electrode part 291 is connected with the electric connector 283 of the electrode fitting shaft 282, the electrode part 291 and electrode fitting shaft 282 will be electrically connected with each other and, when the tip electrode shaft 294 of the electrode part 291 is inserted through the electrode inserting hole 242a of the sheath connecting part 16 and is inserted and fixed at the rear end in the electrode inserting hole 284 of the slider 281, the above mentioned electrode part 291 and slider 281 will be mechanically connected with each other.

The other operations and effects are the same as in the sixth embodiment.

The 11th embodiment of the present invention is shown in FIGS. 21 and 22.

As shown in FIG. 21, a resectoscope apparatus 320 of this embodiment comprises a sheath 321 shown by broken lines, a treating scope 322 inserted through this sheath 321, a handle 323 connected to this treating scope 322 and an electrode device 334 connected to this handle 323 and inserted in a treating tool channel of the above mentioned treating scope 322.

The above mentioned treating scope 322 is provided on the tip side of a body 331 with an observing optical system pipe 333 internally provided with an observing optical system 332, light guide pipes 335 internally provided respectively with light guides 334 and a channel pipe 337 forming a treating tool channel 336 through which treating tools are inserted. By the way, the above mentioned channel pipe 337 is shorter than the other pipes 333 and 335. An eyepiece part 341 is provided, for example, above the above mentioned body 331 and comprises an eyepiece pipe 342a extended upward out of the upper part of the above mentioned body 331, an eyepiece pipe 342b extended rearward from the end of this eyepiece pipe 342a and an eyepiece 343 provided at the rear end of this eyepiece pipe 342b. The above mentioned eyepiece pipes 342a and 342b are internally provided with an optical system transmitting to the above mentioned eyepiece 343 an observed image transmitted by the observing optical system within the above mentioned observing optical system pipe 333. A connecting part 345 which can connect the above mentioned handle 323 is provided at the rear end of the above mentioned body 331.

On the other hand, the above mentioned handle 323 has a connecting part 352 having finger hangers 351a and 351b provided to project above and below and connected to the above mentioned connecting part 345, a guide shaft 353 extended rearward from this connecting part 352, a slider 354 sliding forward and rearward along this guide shaft 353 and a spring 355 mounted between this slider 354 and the above mentioned lower finger hanger 351b and energizing the above mentioned slider 354, for example, rearward. The above mentioned slider 354 is provided with a finger hanging ring 356.

The above mentioned electrode device 334 comprises an electrode driving shaft 361 connected and fixed at the rear end to the above mentioned slider 354 and inserted through the treating tool channel 336 of the above mentioned treating scope 322 and an electrode part 362 connected to this electrode driving shaft 361 at the tip. The above mentioned electrode part 362 comprises an electrode body 363 connected to the above mentioned electrode driving shaft 361, forked electrode shafts 364 extended out of this electrode body 363 and, for example, a loop-like tip electrode 365 mounted between the tips of these electrode shafts 364. By the way, as shown in FIG. 22, the above mentioned electrode shafts 364 are bent to avoid the front of the observing optical system 332 and light guides 334 of the treating scope 322. An electric cable not illustrated electrically connected with the above mentioned tip electrode 365 is inserted through the above mentioned electrode driving shaft 361 and is connected to an electric cord 213 extended from the above mentioned slider 354 and provided at the tip with a connector 214 connected to a high frequency current source not illustrated.

By the way, the means of connecting the above mentioned electrode driving shaft 361 and electrode part 362 with each other may be any of such means as are shown, for example, in the sixth, seventh and ninth embodiments.

According to this embodiment, as compared with the case that an optical sighting tube in which an observing optical system and light guide are contained in one pipe is inserted through a sheath, such space within the sheath as can be used to connect the electrode driving shaft 361 and electrode part 362 with each other can be made larger, therefore, the freedom of the design of the connecting part of the electrode driving shaft 361 and electrode part 362 will increase and the connection will be easy.

The other operations and effects are the same as in the fifth embodiment.

By the way, in the first to 11th embodiments, the electric connecting part of the electric cord and electrode device shaft part may be provided, for example, in front of the connector separately from the connector mechanically connected to the slider.

The 12th embodiment of the present invention is shown in FIGS. 23 to 31.

As shown in FIGS. 23 to 25, a resecting handle 401 comprises an electrode 404 formed integrally of an electrode part 404 and cord part 403, an optical sighting tube inserting part 405 inserting and connecting such optical sighting tube 595 as is shown in FIG. 24, a slider part 4 sliding the electrode 404 forward and rearward and a body 407. As shown in FIG. 23, a plug 410 electrically connectable with a high frequency current source not illustrated by inserting an inserting part 409 is connected at the end of the above mentioned cord part 403 so that the cord part 403 and the high frequency current source not illustrated may be electrically and mechanically connected with each other.

The above mentioned body 407 is shown in FIGS. 25 and 26. The resecting handle 401 can be water-tightly and removably connected with such sheath 502 as is shown in FIG. 25 by a tapered part 415 of a connecting part 414 formed in front of the body 407 and a pin 416 (See FIG. 23). By the way, the above mentioned sheath 502 comprises an elongate hollow tube part 506a insertable into a body cavity and a sheath body 506 consisting of a tubular body connected to this hollow tube part 506a at the base end and communicating with the interior of the above mentioned hollow tube part 506a. The above mentioned sheath body 506 is provided with a water feeding port 507 for injecting a liquid. The hollow tube part 506a is fitted at the tip with a beak 508 made of an insulating material. In the rear of the above mentioned connecting part 414, as shown in FIG. 26, a cover 419 of a substantially square cross-section having a groove 418 having steps 417 and having a rectangular cross-section opened downward is extended to an optical sighting tube connecting part 420 formed at the rear end of the optical sighting tube inserting part 405. A lower finger hanger 421 is provided to project downward from the vicinity of the connecting part 414 so that the middle finger and third finger may be hung in case the resecting handle is held by one hand and an upper finger hanger 422 is provided to project upward so that the index finger may be hung. A spring shaft 424 slidably holding a spring 423 always rearward energizing the slider 406 rearward from the front projects above within the above mentioned groove 418. A guide pipe tube 425 is extended to the optical sighting tube connecting part 420 through the connecting part 415 from the front of the connecting part 415 below within the groove 418. In the optical sighting tube connecting part 420, an optical sighting tube inserting hole 426 having substantially the same inside diameter as of the guide pipe 425, O-ring 427 and O-ring presser 428 fixing this O-ring 427 are adjacently provided in the rear of the guide pipe 425 so that the optical sighting tube 595 may be inserted through the guide pipe 425 while keeping the water-tightness and the optical sighting tube 595 may be led at the tip to the tip of the resecting handle 401.

The above mentioned slider part 429 consists of a slider front part 429 and slider rear part 430 which are made integral by the engagement of snap fits 431 projecting forward out of the slider rear part 430 and holes 432 formed in the slider front part 429 respectively with each other. The upper contours of the slider front part 429 and slider rear part 430 are substantially the same as of the groove 418. A spring hole 433 through which the spring 423 can be inserted and an optical sighting tube pipe hole 434 through which the optical sighting tube pipe 425 can be inserted are formed through the slider front part 429. A shaft hole 435 through which the spring 423 can not be inserted but only the spring shaft 424 can be inserted and an optical sighting tube pipe hole 436 through which the guide pipe 425 can be inserted are formed through the slider rear part 430. The above mentioned slider front part 429 and slider rear part 430 are integrally forward and rearward slidably contained within the groove 418 within the cover 419.

A thumb hanger 437 on which the thumb can be hung in case the resecting handle 401 is held by one hand is provided in the lower rear of the above mentioned slider rear part 430 so that the slider part 406 may be slid forward within the groove 418 against the force of the spring 423 and, when the force of the thumb is released, the slider 406 may be energized by the spring 423 to the optical sighting tube connecting part 420. A pin hole 438 in which a connecting pin 596 of the optical sighting tube 595 (See FIG. 24) can be inserted is provided above the optical sighting tube inserting hole 426 of the above mentioned optical sighting tube connecting part 420 so that, by engaging a groove 597 of the optical sighting tube 595 with a piano wire 440 suspended within a space 439 in front of the pin hole 438, the optical sighting tube 595 can be removably connected to the resecting handle. By the way, a screw 460 is projectably screwed toward the groove 418 from the optical sighting tube connecting part 420 so that the displacement of the slider part 406 within the groove 418 may be adjustable.

Figure 31:
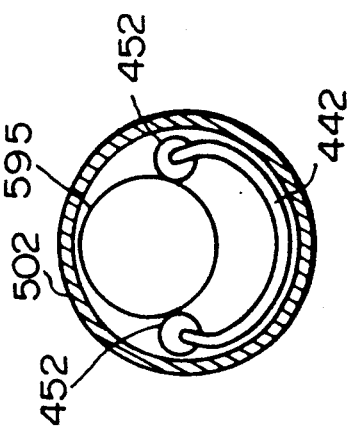
Figure 30:
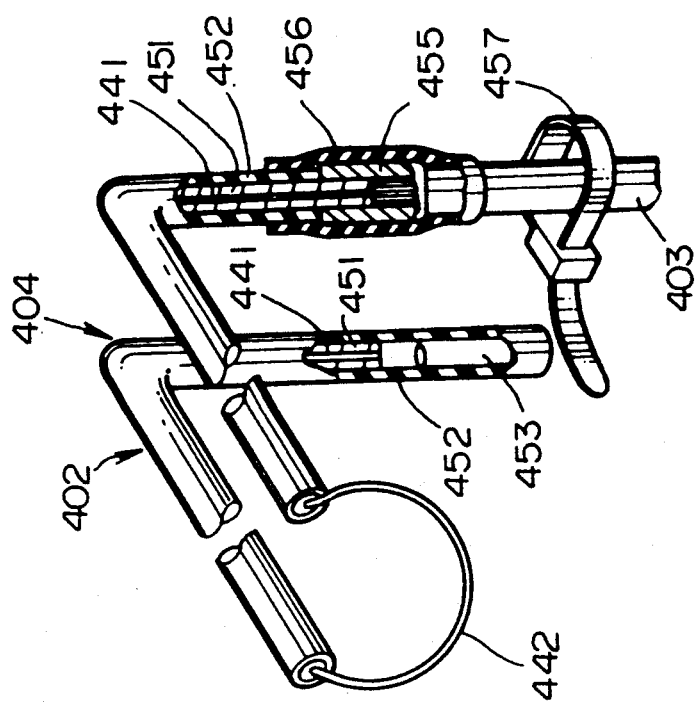
Figure 29:
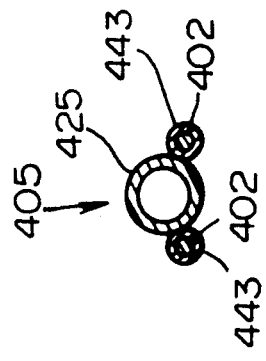

As shown in FIGS. 30 and 31, at the tip of the electrode part 402 projected forward from the tip of the above mentioned optical sighting tube inserting part 405, a wire 441 is formed as exposed along the inner peripheral surface of the sheath 502 as a loop-like loop 442 which can resect tissues within a body cavity when a high frequency current is passed. The above mentioned wire 441 is held by being inserted through guide pipes 443 fixed on both sides of the guide pipe 425 from both ends of the above mentioned loop 442, is further contained in inserting holes 444 formed in the connecting part 414 and O-ring holes 445 communicating with these holes 444, is inserted through O-rings 447 fitted by O-ring pressers 446 fitted to the O-ring holes 445 and is extended to electrode holes 448 and spaces 449 provided in the slider front part 429 of the slider part 406. This wire 441 is bent downward within the spaces 449 and is led to grooves 450 provided between the slider front part 429 and slider rear part 430, is covered with stainless steel pipes 451 except in the loop 442 and is further insulatively coated thereon with Teflon tubes 452.

By the way, as shown in FIG. 30, the wire 441 led to the groove 450 of the slider part 406 is sealed at one end with a plastic 453, is pressed and connected at the other end by a calking pipe 455 as electrically connected with the cord 403 at the end within a space 454 communicating with the lower part of the groove 450 and is further insulatively coated thereon with a thermocontracting tube 456. In the position of the lower end of the above mentioned space 454, a clamp 457 is wound on the cord 403 so that the cord 403 will not be removed even if pulled from below.

Thus, in this embodiment, the electrode and electrode cord are connected with each other within the slider part 406 and the connecting part is insulatively coated with the thermocontracting tube 456 and is watertightly held by the slider front part 429 and slider rear part 430 to be integral with the slider part 406. Therefore, the current leak and contact failure are never likely to occur. That is to say, as all but the electrode tip and current source end is perfectly insulatively coated, there is no electric leak in the intermediate part, there is no such movable part as an electrode fixing mechanism in the slider part 406, the contact is not likely to fail due to any mis-operation and therefore a high electric safety and electric stability can be obtained.

It is apparent that, in this invention, working modes different in a wide range can be formed on the basis of this invention without departing from the spirit and scope of the invention. This invention is not restricted by its specific working modes except being limited by the appended claims.

What is claimed is:

1. A resectoscope apparatus comprising:
   an elongate hollow sheath to be inserted into a body cavity;
   an electrode inserted through said sheath to make such treatments as of resecting and coagulating tissues within the body cavity by using a high frequency current;
   an operating part which can operate said electrode from outside the body;
   a cord for feeding a high frequency current to said electrode from a high frequency current source;
   an optical sighting tube inserted through said sheath and having an optical system which can observe the body cavity interior; and
   a connecting means mechanically removably connecting said electrode shaft part at the rear end to said slider,
   wherein said electrode is made integral at least on the rear end side with said cord, wherein said electrode on the rear end side and said cord are made integral as electrically connected as insulated from outside, wherein said electrode has a shaft part connected at the rear end to said operating part and inserted in said sheath and a tip electrode part provided at the tip of said shaft part and projected and retracted from said sheath tip by the operation of said operating part, wherein said operating part has a connecting part removably connectable to said sheath at the rear end and a slider connected with said electrode shaft part at the rear end and slidable in the axial direction.

2. A resectoscope apparatus according to claim 1 wherein said connecting means has a connector provided at the rear end of said electrode shaft part and a groove provided in said slider and engaged with said connector.

3. A resectoscope apparatus according to claim 2 wherein said connecting part of the operating part has an electrode inserting groove in which said electrode shaft part is insertable from the side.

4. A resectoscope apparatus according to claim further comprising a watertight means engaging with said electrode inserting groove.

5. A resectoscope apparatus according to claim 4 wherein said watertight means includes a packing.

6. A resectoscope apparatus according to claim 4 further comprising a regulating means for regulating a movement of said watertight means relative to a moving direction of said electrode.

7. A resectoscope apparatus according to claim 6 wherein said regulating means includes a regulating groove provided in said connecting part and a regulating projection provided in said watertight means and engaging with said regulating groove.

8. A resectoscope apparatus according to claim 1 further comprising a stabilizer provided in said shaft part of said electrode and coupled to said optical sighting tube.

* * * * *

UNITED STATES PATENT AND TRADEMARK OFFICE
CERTIFICATE OF CORRECTION

PATENT NO. : 5,007,907
DATED : April 16, 1991
INVENTOR(S) : NISHIGAKI et al

It is certified that error appears in the above-identified patent and that said Letters Patent is hereby corrected as shown below:

On the cover page, after [Item 22], the following should appear --[30]    Foreign Application Priority Data
    Sep. 17, 1988 [JP] Japan ................ 63-233321--.

Signed and Sealed this

Twenty-ninth Day of September, 1992

Attest:

DOUGLAS B. COMER

*Attesting Officer*     Acting Commissioner of Patents and Trademarks